(12) United States Patent
Thornton et al.

(10) Patent No.: US 11,534,304 B2
(45) Date of Patent: Dec. 27, 2022

(54) DEVICE FOR RENAL DECONGESTION

(71) Applicant: Troy Thornton, San Francisco, CA (US)

(72) Inventors: Troy Thornton, San Francisco, CA (US); Robert Laduca, Bonny Doon, CA (US)

(73) Assignee: Troy Thornton, San Francisco, CA (US)

( * ) Notice: Subject to any disclaimer, the term of this patent is extended or adjusted under 35 U.S.C. 154(b) by 45 days.

(21) Appl. No.: 16/831,585

(22) Filed: Mar. 26, 2020

(65) Prior Publication Data

US 2020/0222187 A1 Jul. 16, 2020

Related U.S. Application Data

(63) Continuation-in-part of application No. PCT/US2018/054643, filed on Oct. 5, 2018.

(Continued)

(51) Int. Cl.
*A61F 2/24* (2006.01)
*A61B 17/12* (2006.01)
*A61F 2/95* (2013.01)
*A61M 60/135* (2021.01)
*A61M 60/33* (2021.01)
*A61M 60/857* (2021.01)

(Continued)

(52) U.S. Cl.
CPC ...... *A61F 2/2475* (2013.01); *A61B 17/12109* (2013.01); *A61B 17/12136* (2013.01); *A61F 2/2418* (2013.01); *A61F 2/95* (2013.01); *A61M 60/135* (2021.01); *A61M 60/139* (2021.01); *A61M 60/295* (2021.01); *A61M 60/33* (2021.01); *A61M 60/857* (2021.01); *A61M 60/894* (2021.01); *A61F 2250/001* (2013.01)

(58) Field of Classification Search
CPC .................................. A61F 2/24; A61F 2/95
See application file for complete search history.

(56) References Cited

U.S. PATENT DOCUMENTS 4,902,272 A 2/1990 Milder et al.
5,505,701 A 4/1996 Anaya Fernandez de Lomana
(Continued)

FOREIGN PATENT DOCUMENTS

DE 202007019486 U1 2/2013
EP 3010563 A2 4/2016
(Continued)

OTHER PUBLICATIONS

Packwood; A tiny pump that can keep blood flowing after a heart attack; 3 pages; retrieved from the internet (https://europe.medtronic.com/xd-en/transforming-healthcare/EUreka/innovation-articles/blood-flow-pump.html) on Feb. 28, 2020.

(Continued)

*Primary Examiner* — Matthew W Schall
(74) *Attorney, Agent, or Firm* — Shay Glenn LLP

(57) ABSTRACT

Methods and apparatuses for pumping blood within a blood vessel are described. The methods and apparatuses can be used for renal decongestion by pumping blood through the kidney(s), thereby increasing a pressure gradient across the kidney(s). The apparatuses can include one or more inflatable elements that can be repeatedly inflated and deflated to cause a pumping action within the blood vessel. In some embodiments, the one or more inflatable elements are positioned within one or more stents.

15 Claims, 16 Drawing Sheets

Related U.S. Application Data

(60) Provisional application No. 62/569,312, filed on Oct. 6, 2017.

(51) Int. Cl.
*A61M 60/295* (2021.01)
*A61M 60/894* (2021.01)
*A61M 60/139* (2021.01)

(56) References Cited

U.S. PATENT DOCUMENTS

| | | | |
|---|---|---|---|
| 6,210,318 | B1 | 4/2001 | Lederman |
| 6,468,200 | B1 | 10/2002 | Fischi |
| 6,514,226 | B1 | 2/2003 | Levin et al. |
| 6,635,046 | B1 | 10/2003 | Barbut |
| 7,241,273 | B2 | 7/2007 | Maguire et al. |
| 7,329,236 | B2 | 2/2008 | Kesten et al. |
| 7,780,628 | B1 | 8/2010 | Keren et al. |
| 7,867,195 | B2 | 1/2011 | Barbut et al. |
| 7,927,268 | B1 | 4/2011 | St. Germain et al. |
| 8,137,374 | B2 | 3/2012 | Barbut |
| 8,382,695 | B1 | 2/2013 | Patel |
| 8,409,128 | B2 | 4/2013 | Ferrari |
| 8,425,454 | B2 | 4/2013 | Shuros et al. |
| 9,126,008 | B2 | 9/2015 | Kim |
| 9,808,254 | B2 | 11/2017 | Hays et al. |
| 10,363,044 | B2 | 7/2019 | Tal et al. |
| 2002/0107536 | A1 | 8/2002 | Hussein et al. |
| 2004/0210306 | A1 | 10/2004 | Quijano et al. |
| 2009/0099516 | A1 | 4/2009 | Gildoni et al. |
| 2012/0095292 | A1 | 4/2012 | Gunday et al. |
| 2016/0022890 | A1 | 1/2016 | Schwammenthal et al. |
| 2016/0213896 | A1 | 7/2016 | Bacallao |
| 2017/0056574 | A1 | 3/2017 | Pfeifer et al. |
| 2017/0173237 | A1 | 6/2017 | Pfeifer et al. |
| 2022/0001154 | A1 | 1/2022 | Rowe et al. |

FOREIGN PATENT DOCUMENTS

| | | |
|---|---|---|
| WO | WO00/35515 A1 | 6/2000 |
| WO | WO01/097879 A1 | 12/2001 |
| WO | WO02/070039 A2 | 9/2002 |
| WO | WO2011/117566 A1 | 9/2011 |
| WO | WO2016/008521 A1 | 1/2016 |
| WO | WO2016/185473 A1 | 11/2016 |

OTHER PUBLICATIONS

Sayer; Improving renal perfusion pressure: procyrion-aortix; 15 pages; retrieved from the internet (https://www.tctmd.com/slide/improving-renal-perfusion-pressure-procyrion-aortix) on Feb. 28, 2020.

Yehuda; Transcatheter renal venous decongestion (TRVD) in acute decompensated heart failure; Clinical Trials Center, Cardiovascular Research Foundation and Columbia University; 22 pages (Poster Presentation); (year of pub. sufficiently earlier than effective US filing date and any foreign priority date) 2019.

DEVICE FOR RENAL DECONGESTION

CROSS REFERENCE TO RELATED APPLICATION

This application is a continuation-in-part of International Patent Application No. PCT/US2018/054643, filed on Oct. 5, 2018, titled "DEVICE FOR RENAL DECONGESTION," now PCT Publication No. WO 2019/071148, which claims priority to U.S. Provisional Patent Application No. 62/569,312, filed Oct. 6, 2017, and titled "DEVICE FOR RENAL DECONGESTION," the entireties of which are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients who suffer heart failure frequently also experience renal failure, as renal failure can be caused by increased systemic venous congestion as a result of low cardiac output and low blood pressure. Such failure is called cardiorenal syndrome (CRS). Currently, heart failure patients are often treated pharmaceutically with diuretics in an attempt to decrease fluid overload (systemic venous congestion). However, during systemic venous congestion, there is lower-than-normal pressures on the arterial side and higher-than-normal pressures on the venous side of the kidneys. As a result, the kidneys are not able to clear the fluid overload using diuretics because there is not sufficient pressure differential across the kidneys. Accordingly, an alternative treatment for renal congestion is desired.

SUMMARY OF THE DISCLOSURE

Described herein are devices configured to help increase fluid flow through the kidneys and therefore aid in renal decongestion. Advantageously, the devices described herein can provide a mechanical solution to create a greater pressure gradient across the kidneys. This greater pressure gradient can allow improved renal function and/or a better renal response to diuretics.

In general, in one embodiment, a device for renal decongestion includes a hollow stent body having a first end and a second end, a first one-way valve at the first end of the hollow stent body, a second one-way valve at the second end of the hollow stent body, and a balloon configured to fit within the hollow stent body between the first one-way valve and the second one-way valve. The balloon is configured to repeatedly deflate to pull blood through the first one-way valve into the hollow stent body and inflate to push blood through the second one-way valve from the hollow stent body.

This and other embodiments can include one or more of the following features. The stent body can include a covering thereon. The balloon can be configured to be positioned within the hollow stent body after the hollow stent body is positioned within a blood vessel. The balloon can be configured to be positioned within the hollow stent body using a catheter with a guide wire positioned therein. The balloon can be configured to be positioned within the hollow stent body prior to the hollow stent body being positioned within a blood vessel. The balloon can be coupled with an inner surface of the hollow stent body. The balloon can be free-floating within the hollow stent body. The hollow stent body can be configured to transition between an expanded state and a collapsed state. The balloon can be configured to repeatedly deflate and inflate within the hollow stent body in the expanded state. A cross section diameter of the hollow stent body in the collapsed state can be suitably small for entry into a human blood vessel. The device can include an introducer sheath that is configured to constrain an outer diameter of the hollow stent body in the collapsed state. The introducer sheath can be configured to be retracted from the hollow stent body such that the hollow stent body can transition to the expanded state. The balloon can be configured to be repeatedly deflated and inflated by a fluid that is introduced via a catheter. The stent can be self-expandable. The balloon can be a first balloon, and the device can further include a second balloon configured to fit within the hollow stent body between the first one-way valve and the second one-way valve. The second balloon can be configured to repeatedly deflate to pull blood through the first one-way valve into the hollow stent body and inflate to push blood through the second one-way valve from the hollow stent body. The first balloon and the second balloon can be attached to an inner surface of the stent. The first balloon and the second balloon can be positioned along the inner surface of the stent approximately 180 degrees apart from one another. The first balloon and the second balloon can be configured to be inflated at the same time. The first balloon and the second balloon can be configured to touch one another within the stent when inflated. The balloon can be an integral part of a liner positioned along an inner circumference of the hollow stent body.

In general, in one embodiment, a method of decongesting a kidney includes: (1) inserting a device within a blood vessel, the device including a hollow stent body having a first end and a second end, a first one-way valve at the first end of the hollow stent body, a second one-way valve at the second end of the hollow stent body, and a balloon configured to fit within the hollow stent body between the first one-way valve and the second one-way valve; and (2) increasing a pressure differential across the kidney by repeatedly deflating the balloon to pull blood through the first one-way valve into the hollow stent body and inflating the balloon to push blood from the hollow stent body through the second one-way valve.

This and other embodiments can include one or more of the following features. Inserting the device within the blood vessel can include inserting the device within an aorta, a vena cava, a renal artery or a renal vein. Inserting the device within the blood vessel can include inserting the hollow stent body into place within the blood vessel and inserting the balloon into the hollow stent body after inserting the hollow stent body. Inserting the balloon can include guiding the balloon through the blood vessel and within the hollow stent body using a catheter coupled to the balloon and a guide wire threaded within the catheter. Inserting the device within the blood vessel can include inserting the hollow stent body with the balloon positioned therein into the blood vessel. Increasing a pressure differential across the kidney by repeatedly deflating the balloon to pull blood through the first one-way valve into the hollow stent body and inflating the balloon to push blood from the hollow stent body through the second one-way valve can include supplying and removing a fluid to and from the balloon with a catheter. Inserting a device within a blood vessel can include inserting the device into the descending aorta so as to decrease afterload on a left ventricle by decreasing pressure at the first end of the hollow stent body.

In general, in one embodiment, a device for renal decongestion includes a hollow covered stent body having a first end and a second end, a first one-way valve, a second one-way valve, and a balloon. The first one-way valve is at the first end of the hollow stent body. The second one-way valve is at the second end of the hollow stent body. The balloon is within the hollow covered stent body between the first one-way valve and the second one-way valve. The balloon is configured to repeatedly deflate to pull blood through the first one-way valve into the hollow stent body and inflate to push blood through the second one-way valve from the hollow stent body in an antegrade direction.

This and any other embodiments can include one or more of the following features. The balloon can be an integral part of a liner positioned along an inner circumference of the hollow stent body. The liner can be sealed at proximal and distal edges of the hollow stent body. The liner can be positioned along the entire inner circumference of the hollow covered stent body. The device can further include an inflation lumen terminating proximate to the liner. The balloon can be configured to inflate at a frequency of at least 0.5 to 3 times a normal heart rate. The balloon can be configured to inflate at a frequency of about 30-180 inflations and deflations per minute. The device can further include a catheter connected to the hollow covered stent body. The device can further include an occlusion balloon positioned along the catheter. The hollow covered stent body can be configured to transition between an expanded state and a collapsed state. The inflated balloon can include a plurality of lobes.

In general, in one embodiment, a method of decongesting a kidney includes: (1) inserting a device within a blood vessel, where the device includes a hollow covered stent body having a first end and a second end, a first one-way valve at the first end of the hollow covered stent body, a second one-way valve at the second end of the hollow covered stent body, and a balloon within the hollow covered stent body between the first one-way valve and the second one-way valve; (2) increasing antegrade flow through the kidney by repeatedly deflating the balloon to pull blood through the first one-way valve into the hollow covered stent body; and (3) inflating the balloon to push blood from the hollow covered stent body through the second one-way valve.

This and other embodiments can include one or more of the following features. The balloon can be an integral part of a liner positioned along an inner circumference of the hollow covered stent body. Inflating the balloon can include providing inflation fluid between the liner and the inner circumference of the hollow covered stent body. Increasing a flow rate of blood through the kidney by repeatedly deflating the balloon to pull blood through the first one-way valve into the hollow covered stent body and inflating the balloon to push blood from the hollow covered stent body through the second one-way valve can include supplying and removing a fluid to and from the balloon with a catheter. Inflating the balloon can substantially fill a lumen of the hollow covered stent. The method can further include inflating an occlusion balloon within the blood vessel to restrict a flow of blood through the blood vessel while repeatedly deflating and inflating the balloon. The method can further include positioning the occlusion balloon within the blood vessel such that it is on an opposite side of the kidney than the hollowed covered stent body. Inserting the device within the blood vessel can include inserting the device within an aorta, a vena cava, a renal artery or a renal vein. Inserting a device within a blood vessel can include inserting the device into the descending aorta so as to decrease afterload on a left ventricle by decreasing pressure at the first end of the hollow covered stent body. The method can further include removing the device from the blood vessel after increasing antegrade flow.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 14A shows the device in the aorta and accessed through the subclavian artery. FIG. 14B shows the device in the vena cava and accessed through the femoral vein. FIG. 14C shows the device in the aorta and accessed through the femoral artery.

FIG. 15A shows the liner deflated, FIG. 15B shows the liner partially inflated, and FIG. 15C shows the liner fully inflated.

FIG. 16A shows the device with bridge tube. FIG. 16B is a top perspective view of the bridge tube.

FIG. 16C is a bottom perspective view of the bridge tube.

FIG. 17A is a perspective view, and FIG. 17B is a cross-section.

DETAILED DESCRIPTION

Described herein are devices for treating renal congestion and restoring renal function (i.e., to prevent kidney failure). In some embodiments, the devices can act as pumps that can be used to increase the pressure gradient across the kidneys. The devices can function by increasing the renal artery pressure and/or decreasing the renal vein pressure, thereby decongesting the kidneys and allowing the kidneys to function at a normal pressure.

As used herein, the terms "proximal" and "distal" are used with respect to normal blood flow, where "proximal" can refer to a position upstream of normal blood flow while "distal" can refer to a position downstream of normal blood flow. Normally blood flows from the aorta to one of the kidneys through the renal artery, which within the kidney branches into smaller arterioles, and then leaves the kidney via the renal vein to the vena cava.

Although the exemplary devices described herein are in reference to treating renal decongestion, other uses are possible. For example, in some embodiments, the devices described herein can extend, for example, from the renal vein and across the hepatic vein to help depressurize or decompress the liver.

The devices described herein can include various features configured to facilitate pumping of blood within a blood vessel. In some embodiments, the device can include one or more inflatable elements (also referred to as balloons). In some embodiments, the devices can include a balloon catheter, which can correspond to a catheter having one or more balloons coupled thereto. In some embodiments, the devices can include one or more covered stents or stent-grafts, which can correspond to generally tubular-shaped structures having an inner cavity (also referred to as a lumen). In some embodiments, the one or more covered stents can surround the balloon(s) when within the blood vessel.

Non-limiting examples of different devices are described below with reference to FIGS. 1-13C. It should be appreciated that in some embodiments, aspects and features of the examples described herein (e.g., with reference to FIGS. 1-13C) can be combined in any manner. For example, some devices may include aspects of devices describe herein having covered stents and aspects of devices without covered stents.

Figure 1:
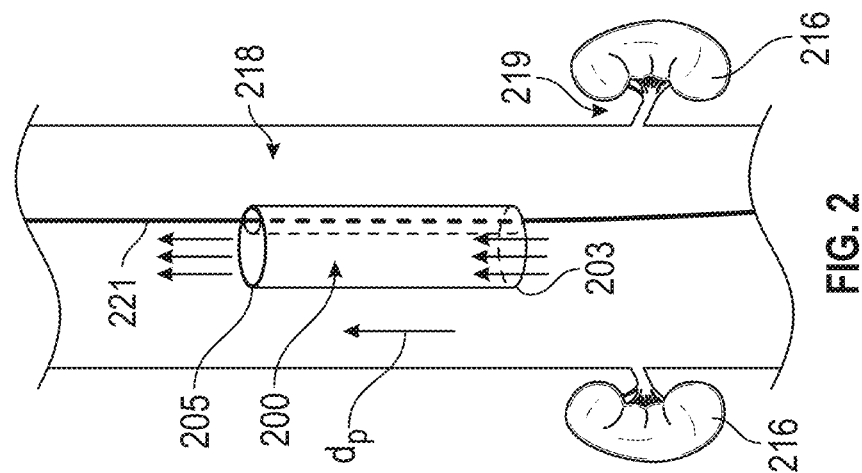
FIG. 1 shows placement of an exemplary device for renal decongestion in the aorta.

In some embodiments, the devices described herein can be placed in the arterial system. For example, as shown in FIG. 1, a device 100 can be placed in the aorta 112. In some cases, the device 100 is positioned proximal to (e.g., just above) the renal arteries 114. In some embodiments, at least a portion of the device 100 can have a generally tubular shape in accordance with the shape of a blood vessel (e.g., aorta 112) and an inner cavity suitable for allowing blood to flow therethrough. An inlet 103 of the device 100 can be positioned proximally (i.e., towards the heart), and an outlet 105 of the device 100 can be positioned distally (i.e., toward the renal arteries 114). The device 100 can act as a pump to pump blood in the direction $d_p$ of normal blood flow, i.e., antegrade from the heart. This can increase the blood pressure flow in the renal arteries 114, thereby creating a greater pressure differential across the kidneys 116. In this way, device 100 may facilitate blood flow through the kidneys 116 and reduce renal congestion. The device 100 can also advantageously decrease afterload on the left ventricle, thereby decreasing the amount of work the heart needs to perform to assist patients with heart failure. The device 100 placed in this manner can act like a temporary left ventricular assist device.

According to some embodiments, the device 100 can be placed within one or both of the renal arteries 114 (e.g., rather than or in addition to within the aorta 112). In some cases, the size (e.g., outer and/or inner diameter) of the device 100 can be adapted to fit within different sized blood vessels. As in the aorta, the pumping action of device 100 within the renal artery(ies) can increase the pressure differential of blood flow across the kidney 116, thereby facilitating blood flow through the kidneys 116. When used on the arterial side (i.e., within the aorta 112 and/or renal arteries 114), the device 100 may have an additional benefit of decreasing "afterload" of the heart, which refers to the pressure against which the heart must work to eject blood during systole. Reducing afterload of the heart can help the left ventricle of the heart recover during contraction.

Figure 2:
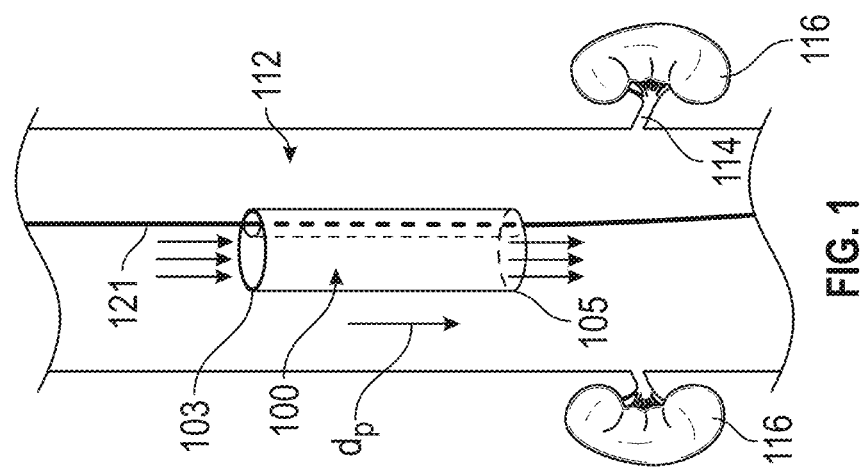
FIG. 2 shows placement of an exemplary device for renal decongestion in the vena cava.

In some embodiment, the devices described herein can be placed in the venous system. For example, as shown in FIG. 2, a device 200 can be placed in the vena cava 218. In some cases, the device 200 is positioned just distal to (e.g., just above) the renal veins 219. The inlet 203 of the device 200 can be positioned proximally and proximate to the renal veins 219, and the outlet 205 can be positioned distally towards the heart. The device 200 can thus pump blood in the direction $d_p$ of normal blood flow, i.e., antegrade to the heart. This can decrease blood pressure flow in the renal veins 219, thereby creating a greater pressure differential across and facilitating blood flow through the kidneys 216. According to some embodiments, the device 200 can be placed within one or both of the renal veins 219 (e.g., rather than or in addition to within the vena cava 218).

Devices 100 and 200 can be positioned within a blood vessel using any technique. As shown in FIGS. 1 and 2, guidewires 121 and 221 may be used to facilitate the positioning of the devices 100 and 200, respectively. In some cases, guidewire 121 or 221 corresponds to a wire, thread and/or spring that is guided through the blood vessel along with the device 100 or 200, respectively. In some embodiments, guidewire 121 or 221 is made of a material suitable for performing procedures on patients, such as a nickel titanium alloy (also referred to as nitinol). In some embodiments, the guidewire 121 or 221 can have pressure-measuring capabilities in order to provide pressure feedback to the physician.

The devices 100 and 200 can be positioned in a blood vessel via any access site. For example, device 100 may be positioned within the aorta 112 or renal artery 114 via a femoral artery. Device 200 may be positioned within vena cava 218 or renal vein 219 via a femoral vein. Alternate access sites for the devices 100 and 200 can be, for example, in the subclavian vein or artery. In such embodiments, the inlet and outlet directions of the devices 100 and 200 may be changed appropriately. For example, returning to FIG. 1, if the device 100 were inserted through a subclavian artery, the inlet 103 and outlet 105 can be oriented as indicated in FIG. 1, and a guide catheter used to place the device 100 may be attached near the inlet 103 of the device 100. Likewise, referring to FIG. 2 if the device 100 were inserted through a subclavian vein, the inlet 203 and outlet 205 can be oriented as indicated in FIG. 2, and a guide catheter used to place the device 200 may be attached near the outlet 205 of the device 200.

FIGS. 3A-3D show side views of an exemplary device 300 that includes a balloon 333 coupled to a catheter 331.

The balloon 333 and catheter 331 can be made of any suitable material. In some embodiments, the catheter 331 is made of a flexible material suitable for insertion within a blood vessel, such as a flexible polymer. In some embodiments, the balloon 333 is made of a polymer (e.g., polyethylene terephthalate (PET), polytetrafluoroethylene (PTFE), polyurethane, and/or nylon) that is suitably flexible for inflation and deflation. In some cases, the balloon 333 is circumferentially positioned around the catheter 331, as shown in FIGS. 3A-3D. The device 300 can be inserted within a blood vessel 302 (e.g., artery, vein, renal artery and/or renal vein) with the aid of a guide wire 321. In some embodiments, the guide wire 321 passes through the inner cavity of the catheter 331 to maintain the orientation and position of the catheter 331 and balloon 333 during insertion.

Figure 3A:
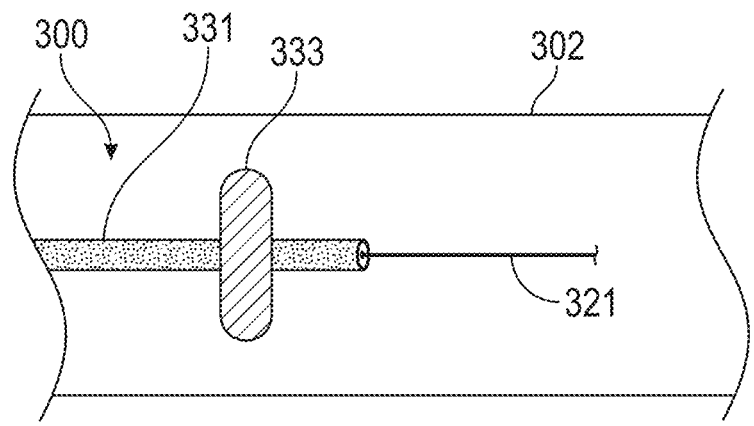
FIGS. 3A-3D show an exemplary device during a renal decongestion procedure.
Figure 3B:
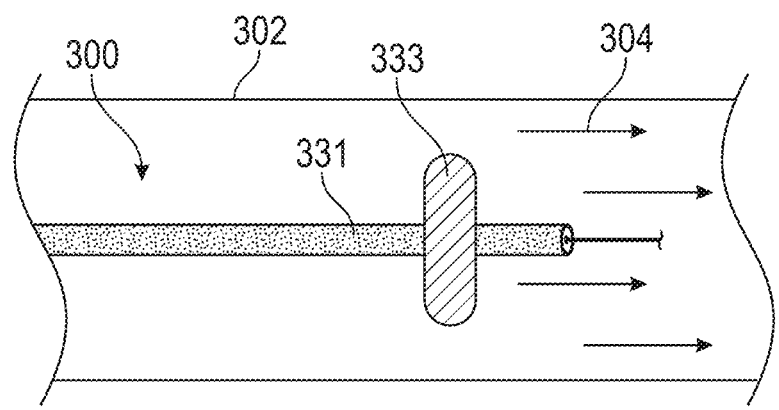

After the device 300 is positioned in the appropriate location within the blood vessel 302 (e.g., as described above with reference to FIGS. 1 and 2), the balloon 333 can be inflated, as shown in FIG. 3A. As shown in FIG. 3B, the catheter 331 with the inflated balloon 333 can then be advanced (e.g., rapidly) in a direction 304 (e.g., in accordance with normal blood flow). For example, if the device 300 is placed in the aorta as shown in FIG. 1, the balloon 333 can be advanced in a direction 304 towards the renal artery 114. As another example, if the device 300 is placed in the vena cava as shown in FIG. 2, the balloon 333 can be advanced in a direction 304 away from the renal vein 219. By (e.g., rapidly) inflating and advancing the balloon 333, the blood within the blood vessel 302 can be pushed (pumped) in the direction of advancement 304, thereby increasing the pressure differential across the kidneys.

Figure 3C:
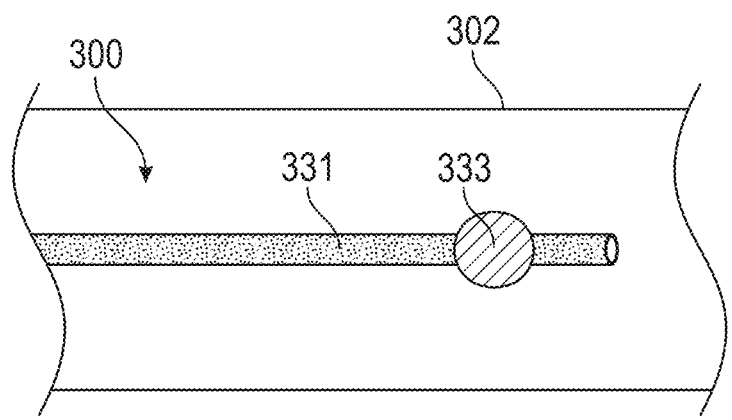
Figure 3D:
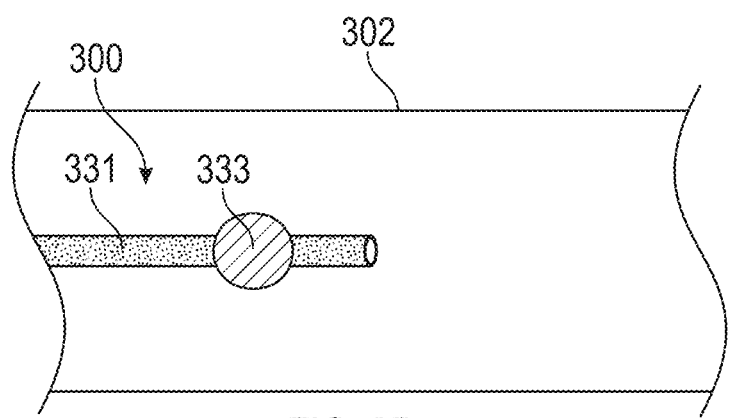

Once the device 300 is advanced (e.g., by a prescribed distance), the balloon 333 can be deflated, as shown in FIG. 3C. The catheter 331 and deflated balloon 333 can then be retracted (e.g., rapidly) in a direction opposite the advancement direction 304 (e.g., opposite normal blood flow), as shown in FIG. 3D. The catheter 331 and balloon 333 can be repeatedly inflated/advanced and deflated/retracted such that the balloon 333 is oscillated back and forth within the blood vessel 302. In this way, the kidneys can experience repeated increases in pressure differential, thereby decongesting the kidney.

In some embodiments, the oscillation of the catheter 331 and balloon 333 can be oscillated a prescribed length (e.g., within a blood vessel and/or within a covered stent) and/or by a prescribed oscillation rate. In some embodiments, the oscillation can occur over a length of at least or at most about 1 centimeter (cm), 1.5 cm, 2 cm, 2.5 cm, 3 cm, 3.5 cm, 4 cm, 4.5 cm or 5 cm. The oscillation can occur over a length ranging between any of the aforementioned values (e.g., 1-5 cm, 1-1.5 cm, 2-4 cm, 3-5 cm, 1-3 cm, 2.5-4.5 cm, 2-5 cm, 1-2 cm, etc.). The oscillation can be achieved by (e.g., rapidly) advancing and retracting the catheter 331 and balloon 333 using any technique. In some embodiments, the oscillation can be activated mechanically, e.g., using a control mechanism on a handle of the catheter. In some embodiments, the oscillation over the prescribed length is at least or at most about 1 to 3 times normal heart rate, i.e., about 60 oscillations/minute up to about 180 oscillations/minute. The oscillation can be computer-controlled, i.e., the device can 300 can include or be connected to a controller to control oscillation. The balloon 333 can have any size and/or shape. In some embodiments, the balloon 333 can be expanded to have a cross section diameter of at least or at most about 0.5 cm to 2 cm, depending on the size of the vessel in which it is to be inflated.

Figure 4:
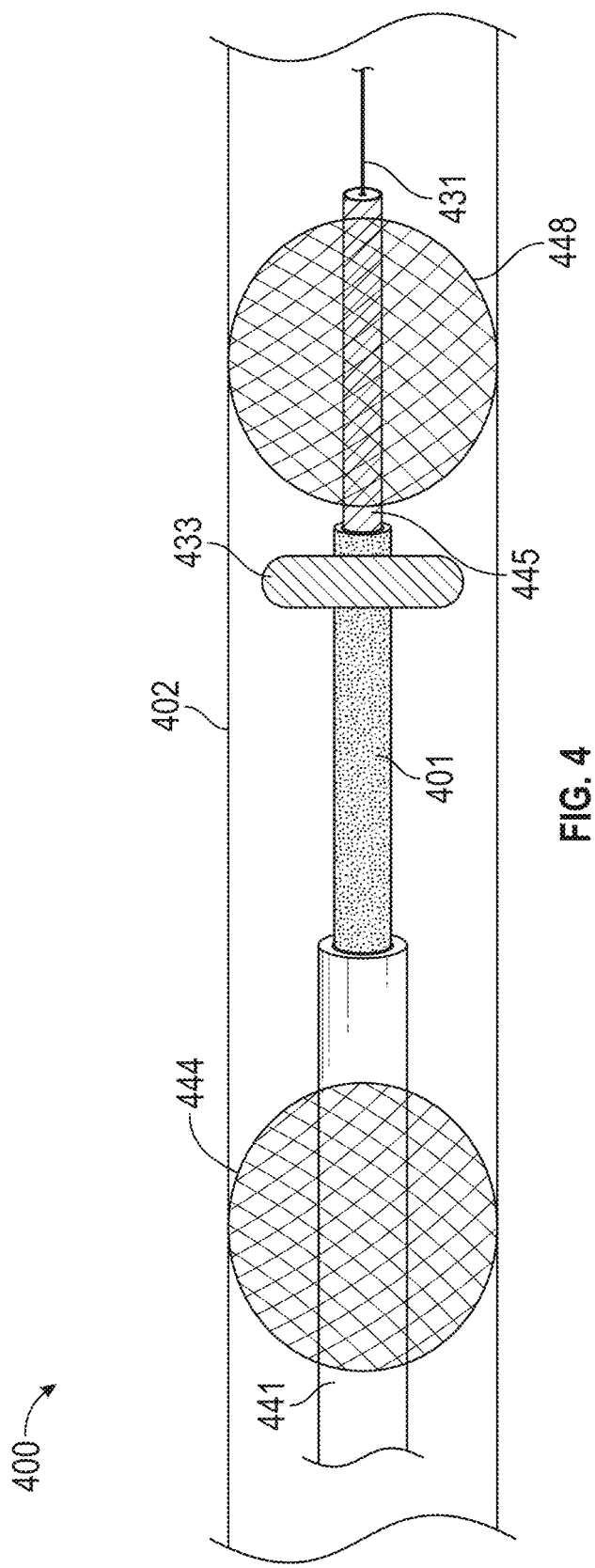
FIG. 4 shows an exemplary device for renal decongestion that includes one or more expandable cages.

In some embodiments, the device includes one or more expandable cages, which can be used to maintain a relative position of the balloon(s). FIG. 4 shows a side view of an exemplary device 400 that includes expandable cages 444 and 448 positioned within a vessel 402. The device 400 can include a catheter 401 with a balloon 433, which can be guided by a guidewire 431 (e.g., similar to device 300) into the blood vessel. Additionally, the device 400 can include an introducer sheath 441 through which the catheter 401 and deflated balloon 433 can be introduced into the blood vessel. The introducer sheath 441 can include an expandable cage 444 coupled thereto (e.g., around the outer diameter of the introducer sheath 441). The expandable cage 444 can be configured to maintain the balloon 433 in a relatively centered position within the blood vessel and reduce damage to the blood vessel wall by the balloon 433 during oscillation. In some embodiments, the expandable cage 444 can be configured to transition between a contracted state (e.g., having a smaller diameter) and an expanded state (e.g., having a larger diameter). For example, the expandable cage 444 may be in the smaller contracted state during insertion within a blood vessel, and in a larger expanded state during oscillation of balloon 433.

In some embodiments, the device 400 can include an inner catheter 445 that is configured to pass through the inner cavity of the catheter 401. The inner catheter 445 can include a second expandable cage 448 coupled thereto (e.g., around the outer diameter of the inner catheter 445). Similar to expandable cage 444, the second expandable cage 448 can be configured to help keep the balloon 433 centered in the blood vessel (e.g., during oscillation). The expandable cage 444 and/or 448 can have any suitable structure and be made any suitable material. In some embodiments, the expandable cage 444 and/or 448 corresponds to a collapsible and expandable mesh or coil structure. The expandable cage 444 and/or 448 can have any size and shape, such as a generally spherical, elliptical or ovoid shape (e.g., when in an expanded state). In some embodiments, one or both of the expandable cages 444 and 448 can be expanded to a have a cross sectional diameter that is equal to or larger than the cross sectional diameter of the balloon 433 in an expanded state. In some embodiments, one or both of the expandable cages 444 and 448 can be expanded to a have a cross sectional diameter that is less than the cross sectional diameter of the balloon 433 in an expanded state.

Figure 9C:
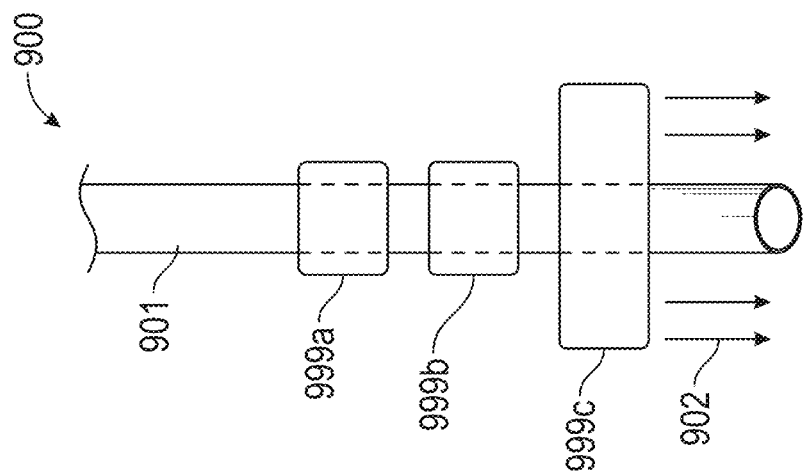
FIGS. 9A-9C show an exemplary device for renal decongestion that includes a plurality of balloons.
Figure 9B:
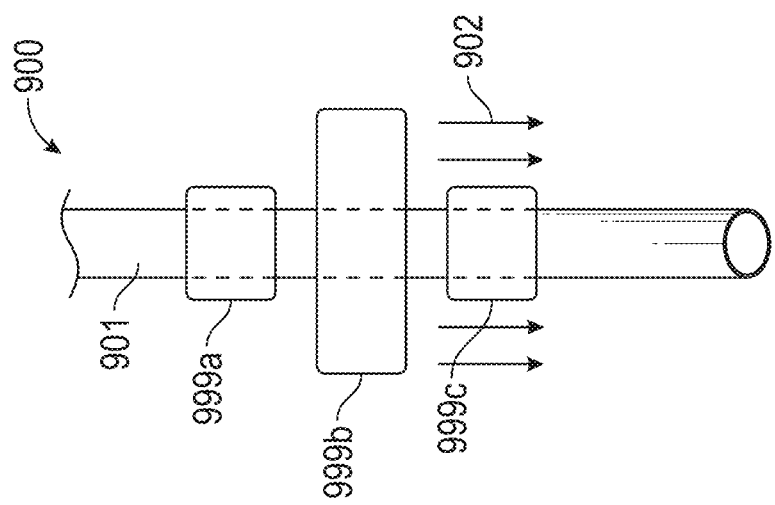
Figure 9A:
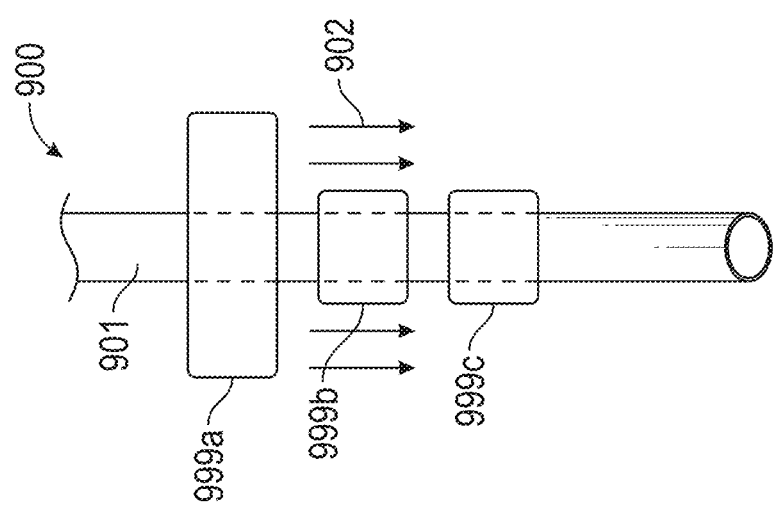

FIGS. 9A-9C show side views of an exemplary device 900 that includes multiple balloons 999a, 999b and 999c. Balloons 999a, 999b and 999c can be coupled in series along the length of the outer diameter of catheter 901. The balloons 999a, 999b and 999c may be configured to inflate and deflate at different times during a renal decongestion procedure. For example, FIG. 9A shows device 900 at a first time when a first balloon 999a is in an inflated state and a second balloon 999b and third balloon 999c are in deflated states. FIG. 9B shows device 900 at a second time when the second balloon 999b is in an inflated state and the first 999a balloon and third balloon 999c are in deflated states. FIG. 9C shows device 900 at a third time when the third balloon 999c is in an inflated state and the first 999a balloon and second balloon 999b are in deflated states. This sequential inflation of balloons 999a,b,c can cause blood to flow in a direction 902 (e.g., from the upstream direction to the downstream direction) to help push blood forward and increase the blood flow in direction 902. In some embodiments, the catheter 901 (with balloons 999a,b,c coupled thereto) can also be moved in the direction 902 and/or opposite to direction 902 to further facilitate the flow of blood in the respective direction(s).

Figure 5A:
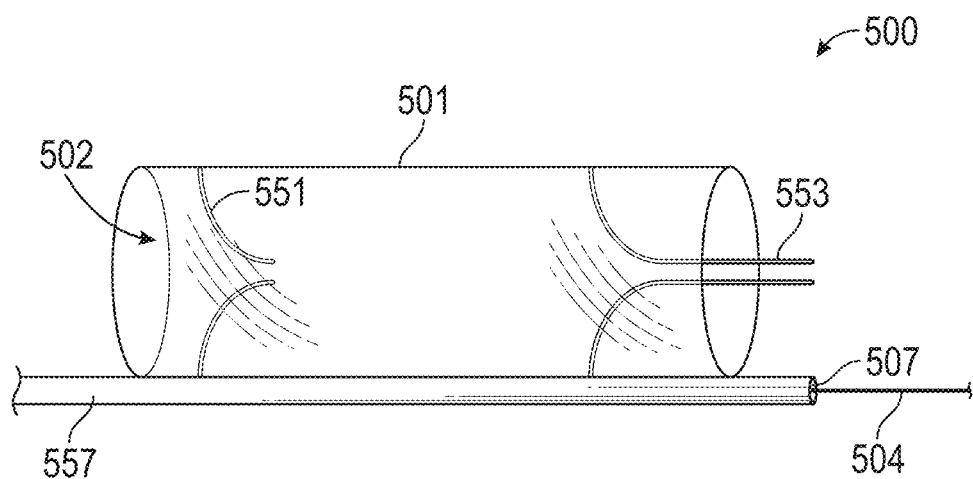
FIGS. 5A-5C show an exemplary device for renal decongestion that includes a covered stent with inlet and outlet valves and an inner balloon.
Figure 5B:
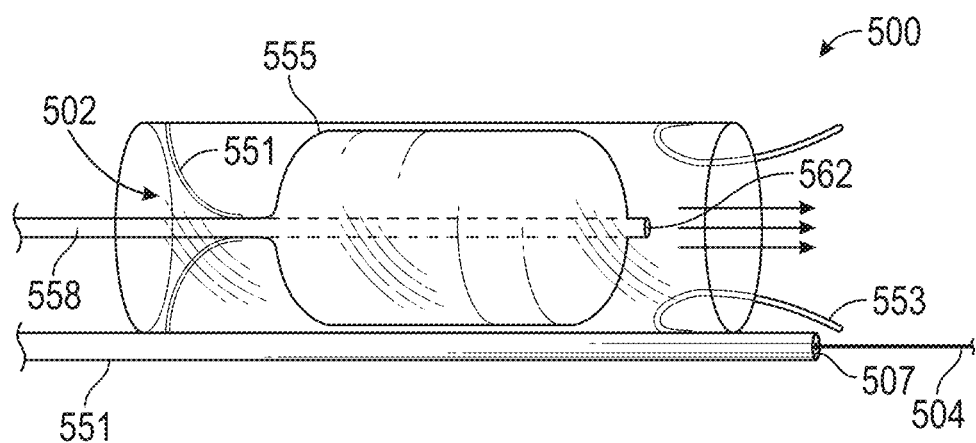
Figure 5C:
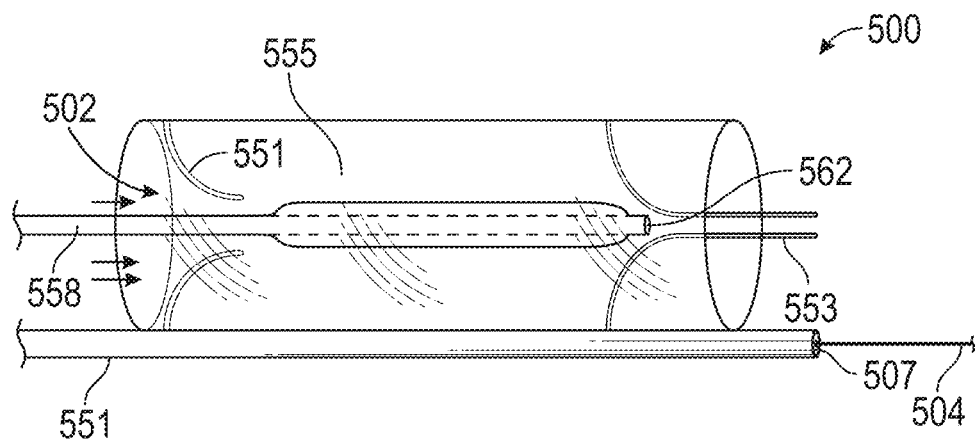

FIGS. 5A-5C shows a device 500 that includes a covered stent 501. The covered stent 501 can correspond to a support structure that has an inner cavity 506 (also referred to as a lumen). The covered stent 501 can have different shapes and/or sizes in accordance with different applications. For example, the stent 501 can have a smaller cross sectional diameter for applications within smaller blood vessels and a larger cross sectional diameter for applications within larger blood vessels. In some embodiments, the covered stent 501 has a generally tubular shape. In some embodiments, the covered stent 501 is a collapsible structure such that the covered stent can collapse into a low profile for insertion and/or removal from a blood vessel, and expand to have a larger diameter within the blood vessel. In some embodiments, the covered stent 501 has a mesh, coil and/or wire structure with a covering thereover. For example, the covering can be made of a fluid-impermeable material (e.g., a polymer material). In some embodiments, the covered stent 501 (e.g., support structure and covering) is made of a metal, polymer and/or fabric material. In some embodiments, the stent 501 is made of a shape-memory metal alloy, such as a nickel alloy, titanium alloy or nitinol.

The size and material of the covered stent 501 can vary. In some embodiments, the covered stent 501 is constructed of a rigid structure (e.g., metal) that forms a supportive frame, and at least a portion of the covered stent 501 is covered by a flexible covering (e.g., which can be made of an air or liquid-impermeable material). The size (e.g., cross sectional diameter and/or length) of the covered stent 501 can depend on the size of the blood vessel. In some embodiments, the covered stent 501 has a length that is designed to maximize and/or optimize the flow rate or pressure change of the renal veins or arteries. In some cases, a covered stent 501 having a longer length and larger diameter can provide a greater flow rate, but may also take longer to fill (e.g., with an inflated balloon therein). In some embodiments, the length of the covered stent 501 can be at least or at most about 5 cm, 10 cm, 15 cm, 20 cm or 25 cm. For example, the length of the covered stent 501 can range between any of the aforementioned values, (e.g., 5-25 cm, 10-20 cm, 5-15 cm, 15-25 cm, etc.). In some embodiments, the covered stent 501 has a prescribed inner diameter (e.g., for accommodating the balloon 555 in an expanded state). In some embodiments, the stent 501 has inner diameter (e.g., when in an expanded state) that is at least or at most about 5-25 mm. In some embodiments, the covered stent 501 has a prescribed outer diameter when collapsed (e.g., to fit within an introducer sheath (e.g., a standard 12-18 Fr inner diameter delivery sheath). In some embodiments, the outer diameter of the covered stent 501 when collapsed can be between 12 Fr and 17.5 F. The outer diameter of the covered stent 501 when collapsed can range between any of the aforementioned values (e.g., 12-14 Fr, 12-14.5 Fr, 13-14 Fr, etc.). In some embodiments, the covered stent 501 can be self-expandable from its collapsed state to its expanded state.

Referring to FIG. 5A, the covered stent 501 can include a first end having a first one-way valve 551 and a second end having a second one-way valve 553. The first valve 551 and second valve 553 can be oriented to form an inlet and outlet. For example, the first one-way valve 551 can be arranged to allow blood to flow 502 within the lumen of the stent 501 without substantially allowing blood to flow out of the stent 501, thereby forming an inlet. Likewise, the second one-way valve 553 can be arranged to allow blood to flow 502 out the lumen of the stent 501 without substantially allowing blood to flow back in the stent 501, thereby forming an outlet. In some embodiments, one or both of the one-way valves 551, 553 are flap valves, wherein flaps 551 (also referred to as leaflets) are configured to open and close depending on the direction of flow.

Referring to FIG. 5B, the device 500 can further include a balloon 555 that is configured to be positioned within the lumen of the stent 501. In some embodiments, the balloon 555 can be coupled with a catheter 558 for insertion within the covered stent 501. The catheter 558 can have in inner lumen 562 that can act as a channel for a fluid (e.g., gas and/or liquid) to travel to and/or from balloon 555 (e.g., for rapid inflation and deflation). In some embodiments, the balloon 555 is positioned within the covered stent 501 while the covered stent 501 is in the blood vessel, followed by insertion of balloon 555 therein. In other embodiments, the balloon 555 is pre-loaded within the covered stent 501 before the device 500 is inserted within the blood vessel. In some embodiments, the balloon 555 is configured to expand the covered stent 501 within the blood vessel. For example, the covered stent 501 can be inserted within the blood vessel while in a retracted (smaller diameter) state. Once positioned, the covered stent 501 can be expanded by inflating balloon 555 therein. In other embodiments, the covered stent 501 can be self-expanding.

When the balloon 555 is deflated the covered stent 501 is expanded (as shown in FIG. 5C), blood can enter the lumen of the stent 501 through the first one-way valve 551 (inlet). When the balloon 555 is inflated (as shown in FIG. 5B), blood within the stent 501 may flow (e.g., symmetrically) outward away from the balloon 555. The balloon 555 can be repeatedly inflated (FIG. 5B) and deflated (FIG. 5C) to continue to push blood forward through the stent 501. In this way, the device 500 can act as a pump that pushes blood in a biased direction within the blood vessel. In some embodiments, the balloon 555 is inflated and deflated in a prescribed manner. For example, in some embodiments, the balloon 555 is inflated at a frequency of at least or at most of about 0.5 to 3 times the normal heart rate, i.e., about 30-240, such 60-180 inflations/deflations per minute. The inflations and deflations can be controlled, for example, with an inflation controller that is part of or connected to the device 500.

As shown in FIGS. 5A-5C, in some embodiments, the covered stent 501 can be attached to a delivery catheter 557 to facilitate the insertion and/or removal of the covered stent 501 within a blood vessel. The guide catheter 557 may be positioned along the outer circumference of the covered stent 501 and coupled with the covered stent 501. A guide wire 504 may run through an inner lumen 507 of the guide catheter 557 to guide the device 500 within the blood vessel.

In some embodiments, at least a portion of the covered stent 501 in which the balloon 555 is inflated (and/or deflated) can itself be expandable (and/or collapsible) (e.g., by contact with the inflating (and/or deflating) balloon 555). For example, the covered stent 501 can be placed within the blood vessel in a collapsed (low profile) state, then be expanded upon inflation of balloon 555 within the blood vessel. A rigid (e.g., metallic) structure of the covered stent 501 can ensure that the expandable portion maintains its shape when the balloon 555 is inflated. In some embodiments, the metallic portion of the covered stent 501 is composed of a shape-memory allow (i.e., nitinol) which allows self-expansion to its enlarged state, and is configured to return to the collapsed state for easier removal from the blood vessel. In some embodiments, this is accomplished by covering at least a portion (e.g., outer surface) of the stent 501 with a sheath (also referred to as an introducer sheath), such as described below with reference to FIGS. 10A-10B.

Figure 6:
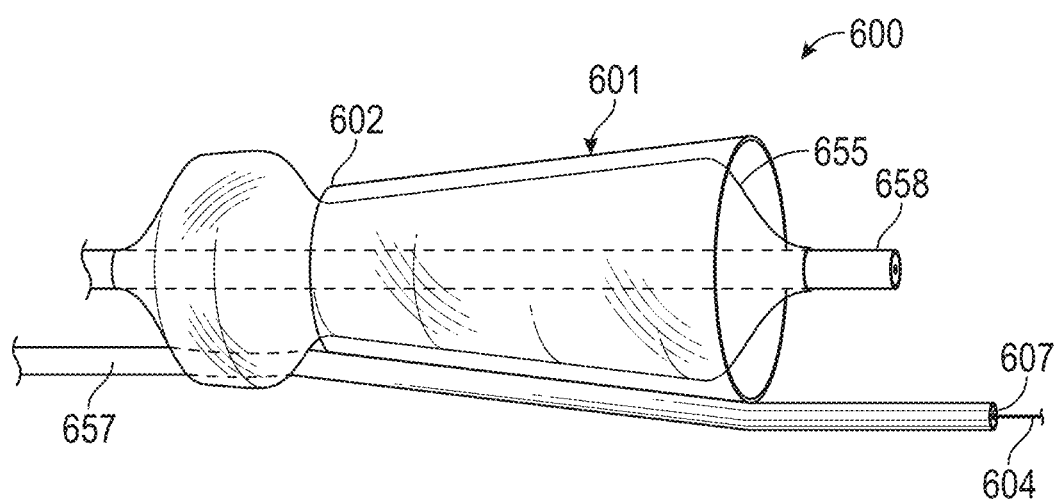
FIG. 6 shows an exemplary device for renal decongestion that includes a conical shaped covered stent.

Referring to FIG. 6, in some embodiments, a device 600 can include a covered stent 601 having a conical shape. By having a conical shape, the balloon 655 can seal against a smaller diameter portion 602 of the stent 601, thereby displacing blood distally. In some cases, the device 600 may not require an inlet valve because the tapered smaller diameter portion 602 can provide proximal sealing during inflation of the balloon 655. In some embodiments, device 600 includes an outlet valve in order to prevent blood flow from returning back into the stent 601 during a pumping operation.

Figure 10A:
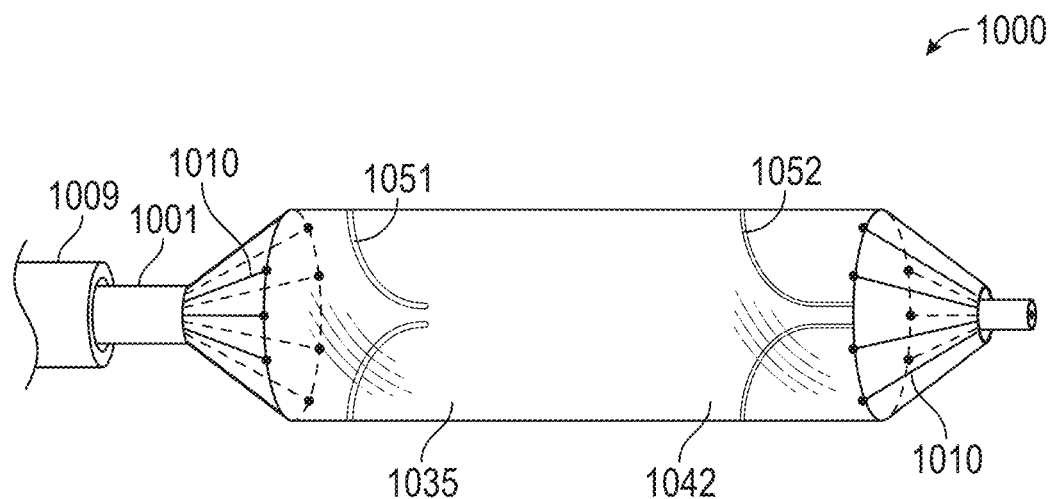
FIGS. 10A-10B show use of an exemplary device for renal decongestion that includes a covered stent and a sheath.
Figure 10B:
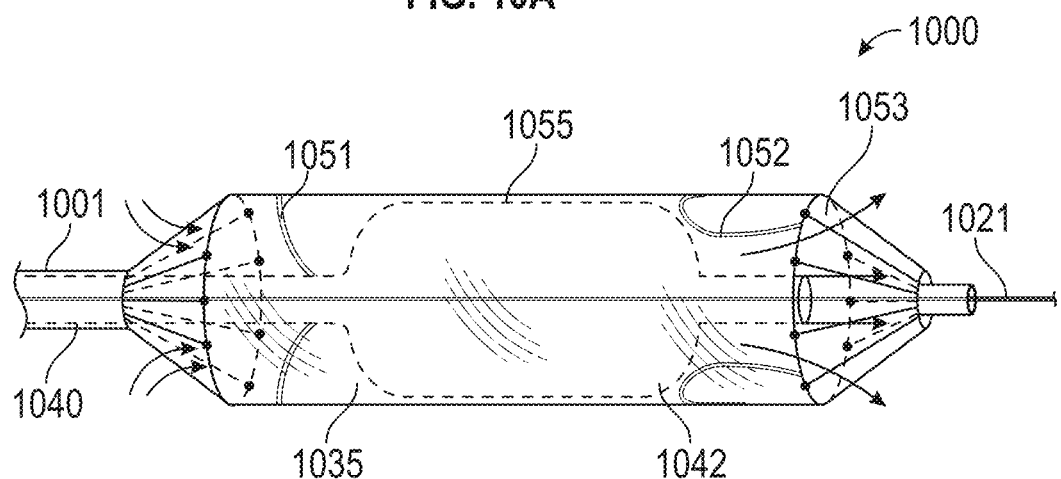

FIGS. 10A-10B show a section view of device 1000 that includes a central delivery catheter shaft 1001 and introducer sheath 1009, in accordance with some embodiments. The sheath 1009 can be made of any suitable material, such as a polymer (e.g., PTFE, PET, Nylon or polyester). The device 1000 can include a covered stent 1035, which can include a collapsible frame coupled to the catheter shaft 1001 with a plurality of wires 1010. During insertion within the blood vessel, an outer surface of the stent 1035 can be covered by the sheath 1009, thereby constraining an outer diameter of the stent 1035 in a low profile configuration. Once delivered to the desired location within a blood vessel, the sheath 1009 can be pulled back such that the sheath 1009 no longer constrains an outer diameter of the stent 1035, thereby allowing the stent 1035 to expand while connected to the wires 1010. Blood can then flow through the wires 1010 (which can be uncovered), through the first one-way valve 1051 (inlet) and into the lumen 1042 of the covered stent 1035.

FIG. 10B shows a balloon 1055 positioned within the lumen 1042 of the expanded stent 1035 between a first one-way valve 1051 (inlet) and a second one-way valve 1052 (outlet) of the covered stent 1035. In some embodiments, the balloon 1055 can by advanced by a catheter 1040 and guided by a guide wire 1021 into the lumen 1042 of the covered stent 1035. The balloon 1055 can then be inflated and deflated, as described herein, to create a pumping action that causes blood to be accelerated and change the pressure differential across the kidneys. After the pumping procedure is complete, the balloon 1055 can be removed from the covered stent 1035 (e.g., facilitated by the catheter 1040 and/or the guide wire 1021). The covered stent 1035 can then be withdrawn back into the sheath 1009 (e.g., by pulling the shaft 1001 coupled thereto), thereby causing the stent 1035 to collapse into the smaller profile such that the entire device 1000 can be removed from the patient's body.

In some embodiments, the shaft 1001 has a lumen with a prescribed inner diameter to accommodate the balloon 1055. In some embodiments, the shaft 1001 can have a lumen with an inner diameter of at least or at most about 7 French gauge (Fr), 8 Fr, or 9 Fr. The shaft 1001 can have a lumen with an inner diameter ranging between any of the aforementioned values (e.g., 7-8 Fr, 8-9 Fr (0.105-0.118 inches), 8-8.4 Fr, 8.8-9 Fr, etc.). In some embodiments, the balloon can have a diameter of at least or at most about 14 millimeters (mm), 14.5 mm, 15 mm, 15.5 mm or 16 mm. The inner diameter of the covered stent 1035 can have an inner diameter ranging between any of the aforementioned values (e.g., 14-16 mm (0.55 inches-0.63 inches), 14-15.5 mm, 14-15 mm, 14.5-16 mm, etc.). In some embodiments, the covered stent 1035 has a prescribed outer diameter, in its collapsed state, to fit within the sheath 1009 as described above (e.g., 12-18 Fr, such as 14-16 Fr).

Figure 7A:
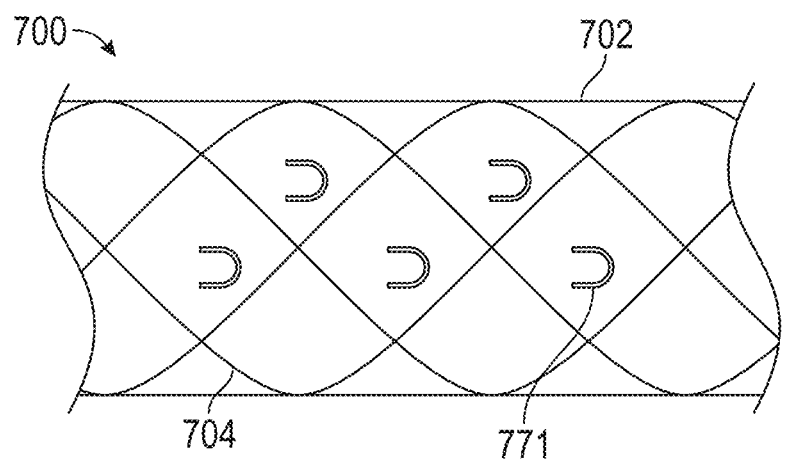
FIGS. 7A-7B show an exemplary device for renal decongestion that includes a covered stent and sheath with flaps that can act as valves.
Figure 7B:
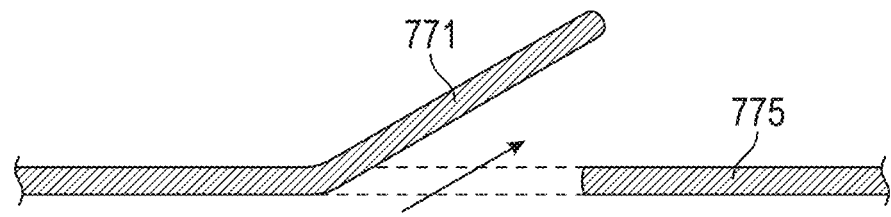

In some embodiments, the devices described herein can includes one or more interior or exterior liners that cover at least a portion of the stent during operation (pumping) of the device. FIGS. 7A-7B shows a portion of a device 700 having a stent 704 (e.g., collapsible and expandable frame) with a liner 702 covering an outer surface of the stent 704. The liner 702 can be made of a conformal material (e.g., conformal polymer sheet). In some embodiments, liner 702 can include one or more flaps 771, which can act as inlet and/or outlet valves during the operation of the device 700. For example, FIG. 7B shows a close-up side section view of the flap 771. Flap 771 can be formed by an opening within the liner 702 such that flap 771 extend from an adjacent portion 775 of the liner 702. The flap 771 can open to allow blood to flow therethrough in a direction as shown in FIG. 7B. The flap 771 can contact the adjacent portion 775 when there is blood flow in the opposite direction, thereby closing the opening. In this way, the flap 771 can act as a one-way valve. The flap 771 can have any shape or size. For example, the flap 771 can have semi-circular and/or chevron shapes. Flaps 771 can be formed using any technique. In some embodiments, flaps 771 are form by cutting correspondingly shaped slits within the liner 702, then heating and/or stretching the flaps 771 such that they overlay the adjacent portion 775 of the sheath 702.

Figure 8:
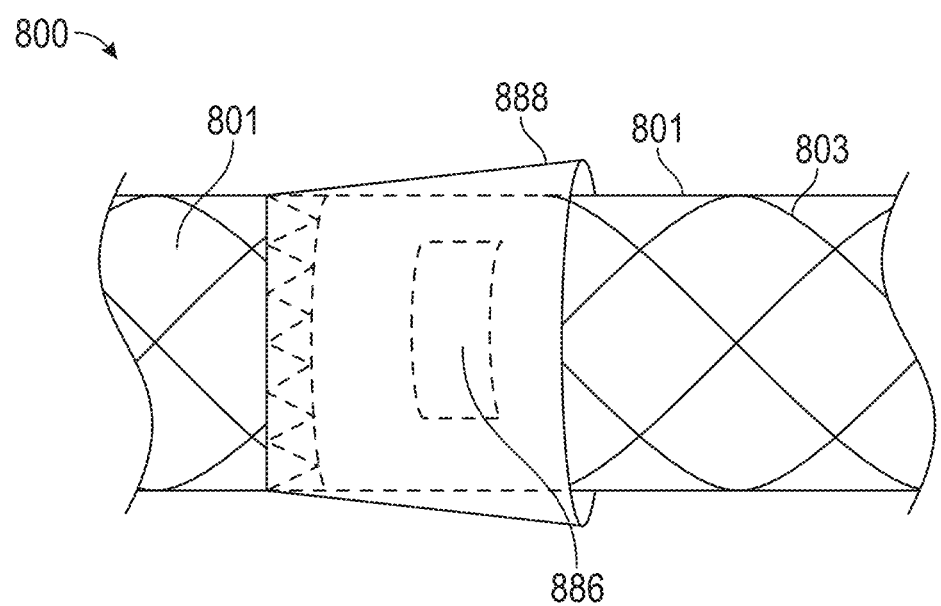
FIG. 8 shows an exemplary device for renal decongestion that includes a covered stent and sheath with a sealing sleeve that can act as a valve.

In some embodiments, the liner includes one or more sealing sleeves that can be used in addition to or instead of flaps. To illustrate, FIG. 8 shows another exemplary device 800 that includes a sealing sleeve 888 bonded to an outer portion of the liner 801, which covers stent 803. The sealing sleeve 888 can be made of a flexible material that is expandable under pressure, and/or can be shaped like a truncated cone (with the distal end larger than the proximal end). The sealing sleeve 888 can be positioned over a hole 886 within the sleeve 801. When internal pressure is created within the device 800, such as when the balloon is inflated, sealing sleeve 888 can be configured to expand, thereby opening the hole 886 and allowing blood to flow therethrough. When there is less internal pressure within the device 800 than outside of the device 800, such as when the balloon is deflated, the sealing sleeve 888 can be configured to seal down against the underlying sheath 801 to cover and close the hole 886, thereby stopping blood from therethrough. In this way, the sealing sleeve 888 can act as an outlet valve that allows blood to flow out of the device 800 and prevent blood from flowing into the device 800. In some embodiments, sheath 801 can include a plurality of sealing sleeve 888 (e.g., around the circumference of the sleeve 801 and/or along the length of the sleeve 801) and a plurality of holes 886 around the circumference and/or along the length of the device 800. In some embodiments, the device additionally or alternatively include one or more flexible sealing sleeve 888 coupled to the inside of the stent and acting as an inlet valve.

Figure 11:
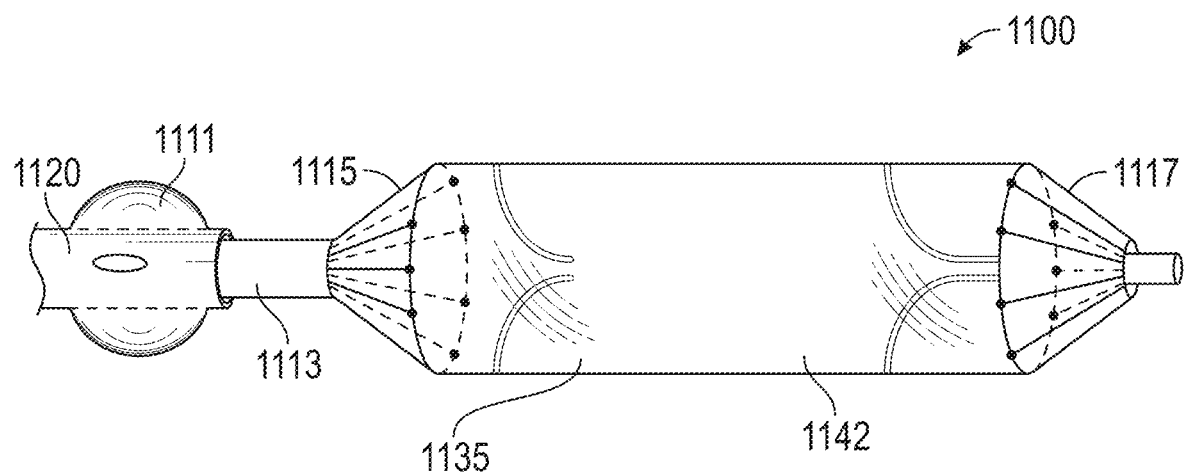
FIG. 11 shows an exemplary device for renal decongestion that includes a covered stent and an additional balloon.

Any of the devices described herein can include one or more occlusion balloons. To illustrate, FIG. 11 shows an exemplary device 1100, which includes an occlusion balloon 1111 positioned on a catheter 1120 that is positioned around the catheter 1113 connected to the stent 1135. As in other embodiments described herein, the stent 1135 can include a lumen 1142 configured to hold a balloon therein for control of flow (e.g., pumping of blood) therethrough. The occlusion balloon 1111 can be positioned proximal to an inflow area 1115 of the device or at an outflow area 1117 of the device 1100 (depending upon the placement and access method) such that the renal veins or arteries are positioned between the device 1100 and the occlusion balloon 1111. This arrangement can allow the occlusion balloon 1111 to selectively and/or variably inflate to restrict the flow of blood, thereby enhancing the ability to increase or decrease the pressure gradient across the kidneys.

Figure 14B:
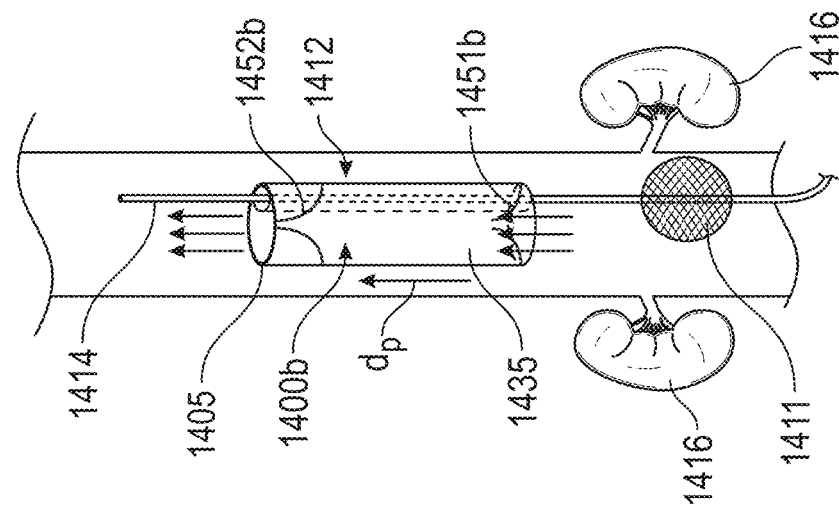
FIGS. 14A-14C show another exemplary device for renal decongestion in place in the blood vessels.
Figure 14A:
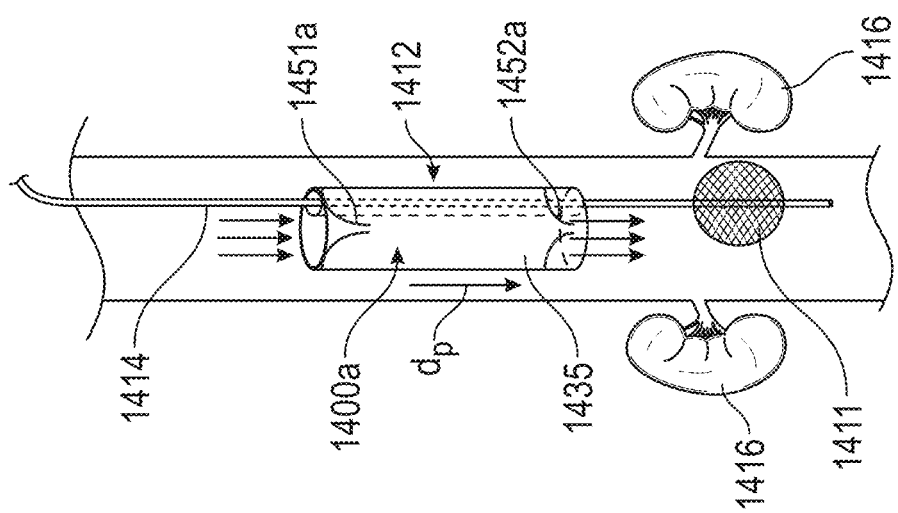
Figure 14D:
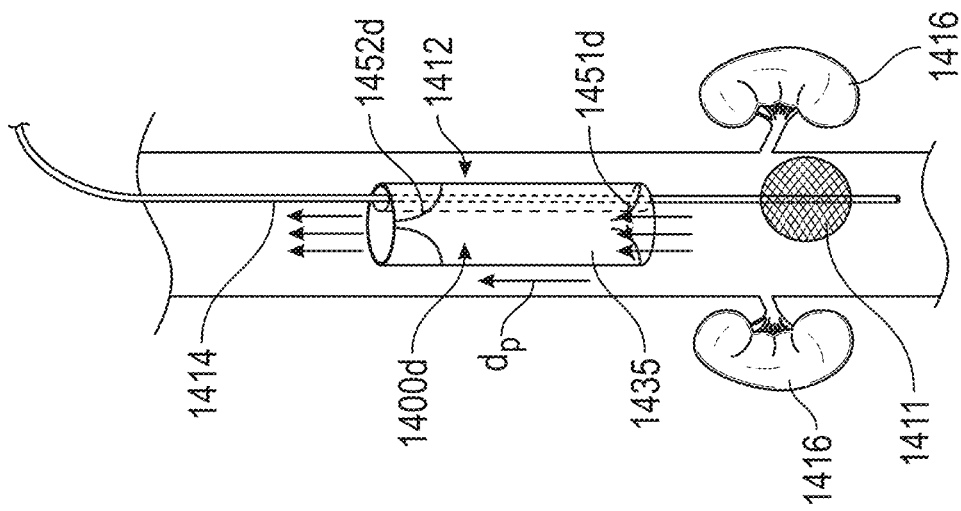
FIG. 14D shows the device in the vena cava and accessed through the subclavian vein.
Figure 14C:
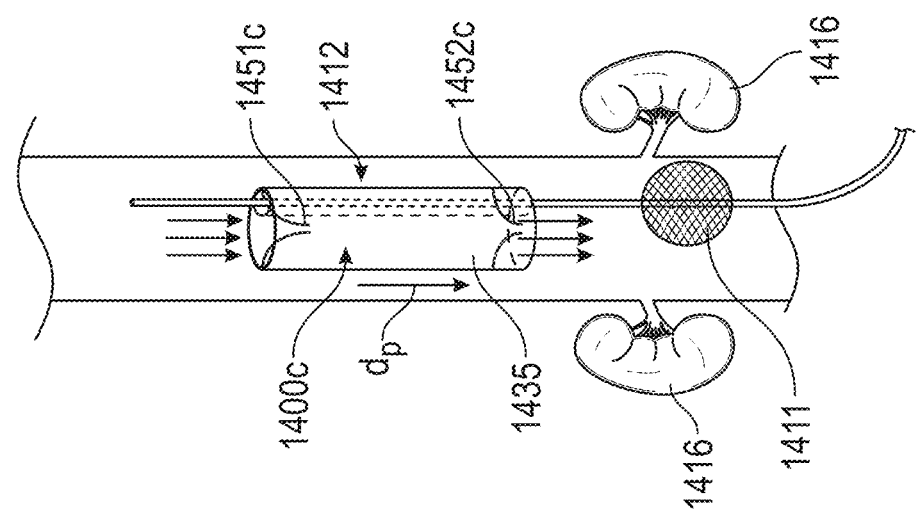

FIGS. 14A-14D show a device 1400 similar to device 1100 implanted within the vessel 1412. FIG. 14A shows the device 1400a in place within the aorta and accessed via the subclavian artery (i.e., via access catheter or guidewire 1414). The occlusion balloon 1411 is positioned on the opposite side of the kidneys 1416 as the covered stent 1435. Further, the inlet valves 1451a and outlet valves 1452a are positioned so as to allow blood to flow therethrough and towards the kidneys 1416 and the occlusion balloon 1411 with the occlusion balloon 1411 at least partially restricting blood flow beyond the kidneys 1416 (i.e., so as to allow more blood to flow into the kidneys 1416). FIG. 14B shows the device 1400b in place within the vena cava and accessed via the femoral vein. The occlusion balloon 1411 is positioned on the opposite side of the kidneys as the covered stent 1435. Further, the inlet valves 1451a and outlet valves 1452b are positioned as to allow blood to flow therethrough away from the kidneys 1416. FIG. 14C shows the device 1400c placed in the aorta via femoral artery access while FIG. 14D shows the device 1400d placed in the vena cava via subclavian vein access.

Figure 12A:
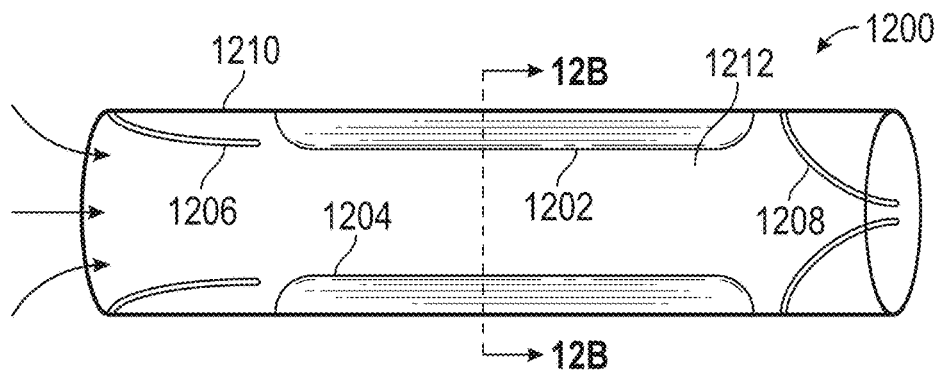
FIGS. 12A-12D show an exemplary device for renal decongestion that includes a covered stent with integral balloons.
Figure 12B:
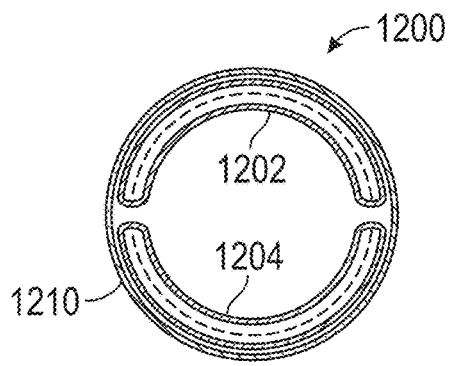

According to some embodiments, the device includes a covered stent having one or more integral balloons (i.e., the one or more integral balloons can have an inflatable space that is formed on one side by the interior surface of the covered stent and on the other side by a liner that is bonded to or part of the interior surface of the covered stent). FIGS. 12A and 12B show a longitudinal section view and a cross section view, respectively, of an exemplary device 1200 having a stent 1210 with a first integral balloon 1202 and a second integral balloon 1204. The first and second integral balloons 1202, 1204 can be positioned within the lumen 1212 of the stent 1210 between a first 1206 one-way valve (inlet) and a second one-way valve 1208 (outlet). The first and second integral balloons 1202, 1204 can be made of any material, such as a relatively conformal material (e.g., conformal polymer). In some cases, the outer surfaces of the first and second integral balloons 1202, 1204 can have a shape (e.g., curved) such that they cooperate to form a shape (e.g., cylindrical) in accordance with the inner surface of the covered stent 1210. In other embodiments, outer surfaces of the integral balloon(s) have shape(s) different than the inner surface of the covered stent (e.g., approximately 180 degrees apart from one another). In some embodiments, the first and second integral balloons 1202, 1204 are coupled to a surface within the covered stent 1210. In some embodiments, the first and second integral balloons 1202, 1204 can be replaced with two free-floating balloons (e.g., cylindrical balloons) within the lumen 1212 of the covered stent 1210 (e.g., held in place by a catheter used for inflation/deflation of the balloons).

Figure 12C:
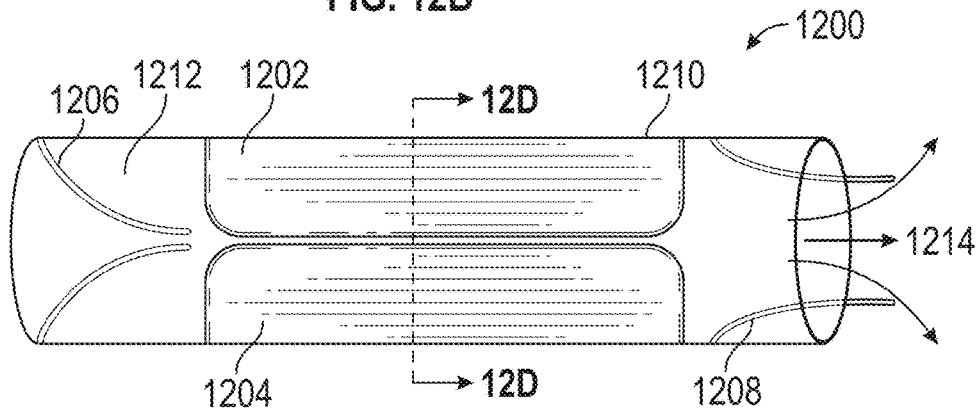
Figure 12D:
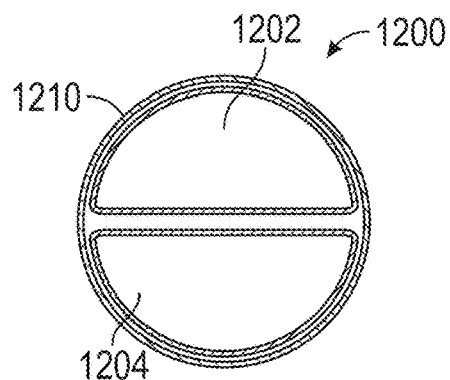

FIGS. 12A and 12B show device 1200 when the first 1202 and second 1204 integral balloons are deflated and blood flow can freely move in the first one-way valve 1206 and into the lumen 1212. FIGS. 12C and 12D show a longitudinal section view and a cross section view, respectively, of device 1200 when the first and second integral balloons 1202, 1204 are inflated. When inflated, the first and second integral balloons 1202, 1204 can increase the pressure within the covered stent 1210, which can cause the first (inlet) one-way valve 1206 to close while the second (outlet) one-way valve 1208 opens to allow blood to flow out of the covered stent 1210 in the direction 1214. In some embodiments, the first and second integral balloons 1202, 1204 are configured to contact each other when inflated to fully displace the blood therebetween. In some embodiments, the first and second integral balloons 1202, 1204 are configured to have a (e.g., minimal) space between each other when inflated.

After inflation, the first and second integral balloons 1202, 1204 can be deflated again (FIGS. 12A-12B) such that blood is pulled (sucked) back into the lumen 1212 of the covered stent 1210 via the first (inlet) one-way valve 1206. During operation of device 1200 within the blood vessel, the first and second integral balloons 1202, 1204 can be repeatedly deflated (FIGS. 12A-12B) and inflated (FIGS. 12C-12D) to repeatedly push blood in the direction 1214. In this way, the device 1200 can act as a pump to increase the pressure differential across the kidneys, as described herein.

In some cases, the first and second integral balloons 1202, 1204 can each have a D-shaped cross section when inflated, as shown in the cross section view of FIG. 12D, such that the flat sides of the first and second integral balloons 1202, 1204 meet each other at a central region of the stent 1210. It should be appreciated that the integral balloon(s) can have any cross section shape and are not limited to the "D-shape" show in FIGS. 12A-12D. For example, if three or more balloons are used, the balloons can have a triangular (pie-piece) cross-sectional shape. As another example, if two or more balloons are used, the balloons can each have a cylindrical shape. In some embodiments, the integral balloons 1202, 1204 can be attached to or formed at least in part by a liner or covering on the inside or outside of the stent 1201.

Figure 13A:
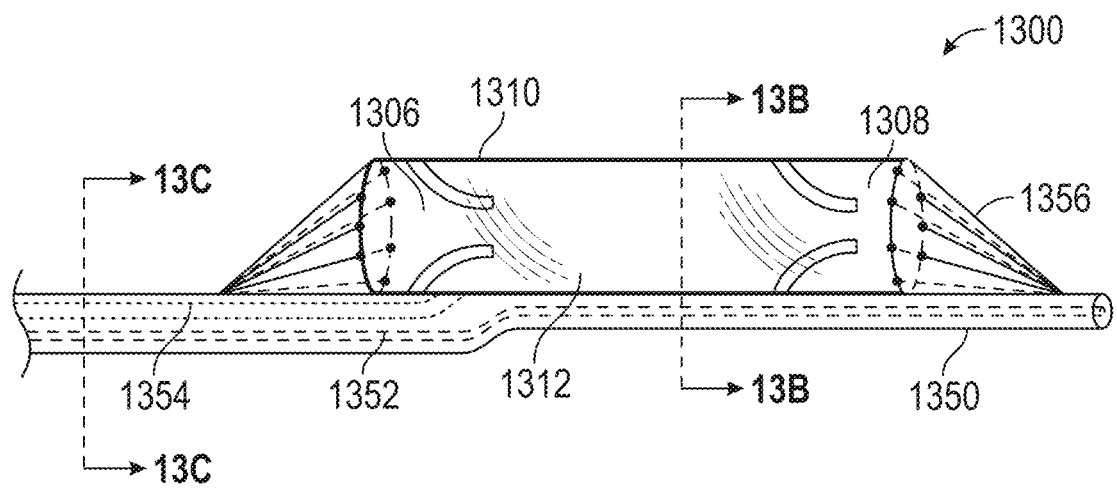
FIGS. 13A-13C show another exemplary device for renal decongestion that includes a covered stent with integral balloons.
Figure 13B:
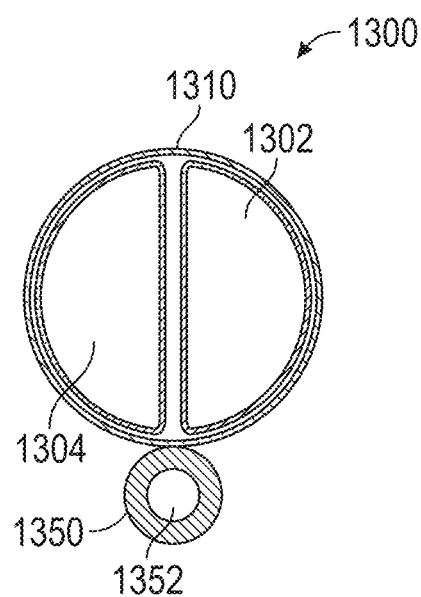
Figure 13C:
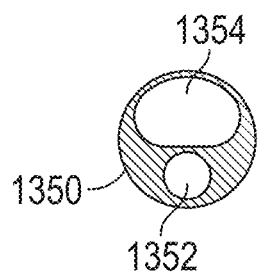

FIGS. 13A-13C show another exemplary device 1300 having a first integral balloon 1302 and a second integral balloon 1304 within covered stent 1310. As with the device 1200 (FIGS. 12A-12D), the first and second integral balloons 1302, 1304 can be positioned between first and second one-way valves 1306, 1308 within the stent 1310. As shown in the longitudinal section of FIG. 13A, the stent 1310 can be coupled to a catheter 1350 having a first lumen 1352 (also referred to as a guide wire lumen) and a second lumen 1354 (also referred to as an inflation/deflation lumen). In other embodiments, the guide wire lumen 1352 and inflation/deflation lumen 1354 are positioned within separate (e.g., two) catheters. The guide wire lumen 1352 can be used to position a guide wire therein. The inflation/deflation lumen 1354 can be fluidically coupled with the one or more integral balloons within the stent 1310 to provide a pathway for fluid (e.g., air and/or liquid) to inflate and deflate the integral balloons 1302 and 1304. The guide wire lumen 1352 and inflation/deflation lumen 1354 can have any size and shape. The cross section views of FIGS. 13B and 13C show the guide wire lumen 1352 and inflation/deflation lumen 1354 having a substantially round, elliptical or oval cross section. In some embodiments, the cross section of the guide wire lumen 1352 is larger than or equal to that of the inflation/deflation lumen 1354 lumen. In some embodiments, the cross section of the guide wire lumen 1352 is less than that of the inflation/deflation lumen 1354 lumen.

In some embodiments, the catheter 1350 is coupled to an outer surface of the covered stent 1310 (i.e., outside of the lumen 1312 of the stent 1310). In some embodiments, the covered stent 1310 is coupled to proximal and distal ends of the catheter 1350 using one or more wires 1356 (e.g., made of metal (e.g., nitinol) or polymer). This can facilitate collapsing of the stent 1310 into an introducer sheath for insertion and removal of the stent 1310 to and from the blood vessel.

In some embodiments, the device 1300 can include only a single integral balloon 1302 or 1304. The single integral balloon 1302 or 1304 can be configured to inflate entirely across the circumference of the lumen 1312. In such embodiments, the integral balloon can be formed of a liner that extends only half way along the inner circumference of the stent. Alternatively, the integral balloon can be a cylindrical liner bonded along half of its circumference so as to enable inflation of only half of the liner.

Figure 15A:
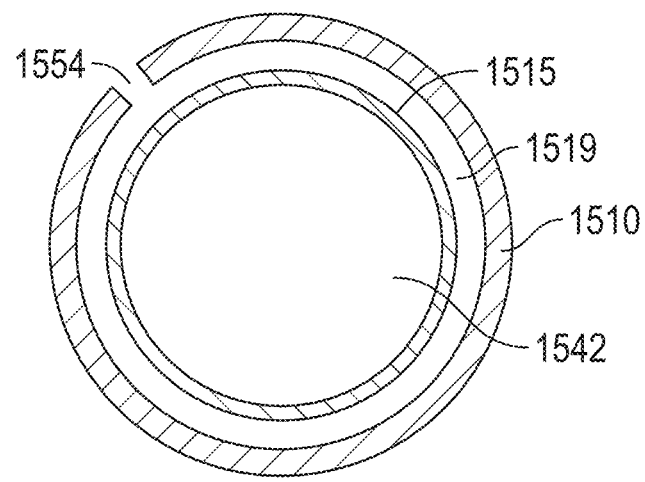
FIGS. 15A-15C show another exemplary device for renal decongestion including an integral balloon formed by a liner.
Figure 15B:
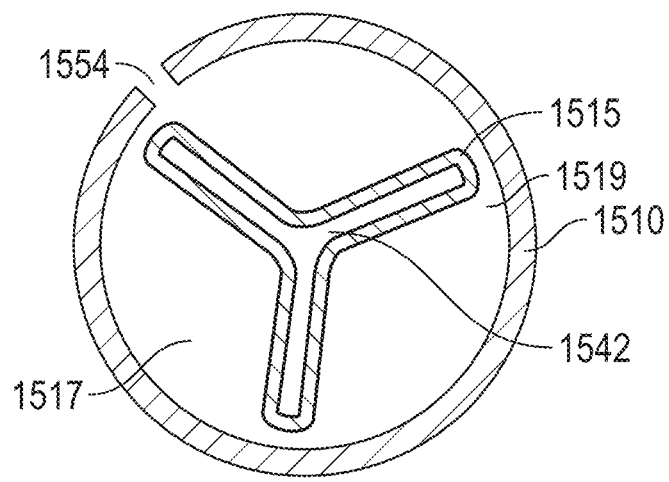
Figure 15C:
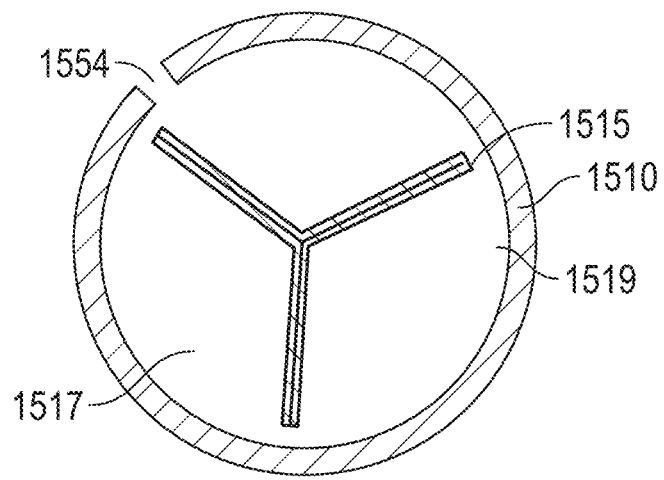

Referring to FIGS. 15A-15C, according to some embodiments, the fluid-impermeable covering of the stent can be used as an integral balloon (e.g., instead of or in addition to the first and second integral balloons 1302, 1304). For example, if the stent 1510 is made of or includes a fluid-impermeable material (e.g., substantially impermeable to air and/or liquid) and is lined with an additional fluid-impermeable liner 1515, the liner 1515 may be configured to expand and move toward a center region of the stent 1510 (i.e., center of the lumen 1542) to displace the blood from therein. The resulting integral balloon (formed by the liner 1515 and the internal surface of the stent 1510) can be substantially tubular or cylindrical in shape. The fluid-impermeable liner 1515 can be coupled to an internal surface of the stent 1510 and sealed around the proximal and distal edges of the stent 1510, but can otherwise be unbonded (or only bonded in a few additional locations) to the stent 1510, thereby creating a space 1519 for inflation. An inflation/deflation lumen 1554 may terminate between the internal surface of the stent 1510 and the liner 1515 such that, when fluid is forced therein, the fluid-impermeable liner 1515 expands and move toward the center of the lumen 1542 to displace the blood (as shown in the transition from FIGS. 15A to 15B and 15C).

Referring to FIGS. 15B and 15C, in some embodiments, inflation of the liner 1515 can cause a plurality of lobes 1517 to form in the liner 1515 such that the lobes 1517 meet in the center of the lumen 1542 to substantial fill the lumen 1542. That is, axial creases can form in the liner 1515 so as to form a plurality of lobes 1517, such as 2-4 lobes, such as 3 lobes. The lobes 1517 can have, for example, a substantially triangular (pie-piece) cross-sectional shape. In some embodiments, the liner 1515 can be configured to form the creases without pre-set creases. In other embodiments, the liner 1515 can include pre-formed axial creases (such as a pre-bent crease, a crease of thicker material, and or a crease that is bonded to the interior surface of the stent 1510). Such a pre-formed crease may advantageously ensure that the lobe number and size are consistent. In some embodiments where the fluid-impermeable liner is used as the integral balloon, the liner 1515 can include multiple sheets of polymeric material, and air can be supplied therebetween.

Figure 17A:
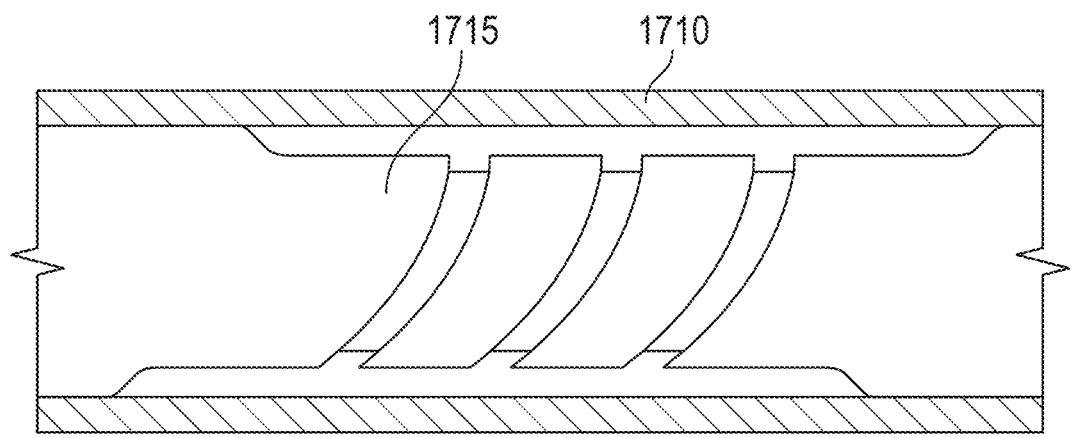
FIGS. 17A-17B show a liner for increased inflation fluid flow.
Figure 17B:
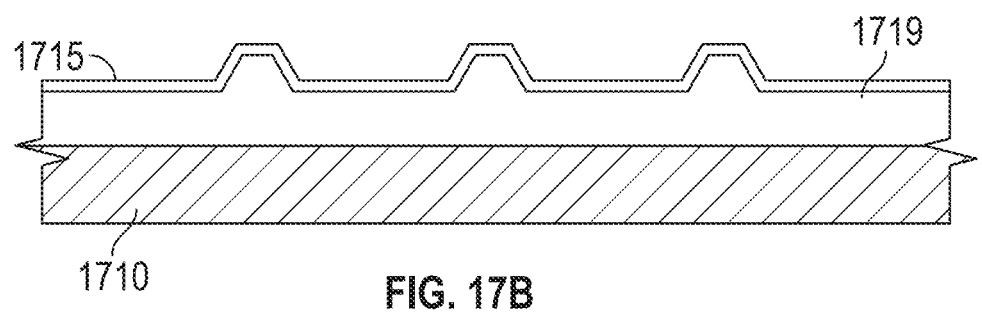

In some embodiments, the liners and/or balloons described herein can be specifically designed to increase the inflation and deflation time thereof (thereby helping to increase the pumping and/or flow rate of blood through the device). For example, the gap between the liner and the stent can have stand-offs or other elements therein to ensure that the gap has a minimum thickness of 0.5 mm-2 mm (e.g., to allow inflation fluid to flow quickly and evenly into and out of the gap). As another example, referring to FIGS. 17A-17B, the liner 1715 can include preformed circumferential ridges or valleys therein. The circumferential ridges can provide multiple pathways for the inflation fluid to flow in and out thereof (e.g., into the space 1719 between the liner 1715 and the stent 1710) and can ensure that the inflation fluid flow evenly along the bladder. The circumferential ridges can also advantageously help ensure that the inflation fluid is fully removed from the balloon, ensuring full deflation of the balloon.

In other embodiments, the liner or balloon can be configured to preferentially inflate first on the inflow end of the device and then sequentially down the length towards the outflow end. For example, the liner or balloon can have a thinner wall (e.g., 0.004"-0.008") at the inflow end and a thicker wall (e.g., 0.012"-0.024") at the outflow end. The thickness of the balloon or liner can gradually increase or increase stepwise from the inflow end to the outflow end. The thinner wall at the inflow end can therefore inflate faster than the thicker wall at the outflow end. Having the inflow end inflate before the outflow end can advantageously increase the flow rate of fluid through the device by increasing the momentum of the fluid in the desired direction during the pressure cycle. Having the inflow end inflate before the outflow end can also advantageously minimize the volume of blood that is trapped between the balloon and the inflow valve, which can in turn advantageously reduce stress on the valve.

Figure 16A:
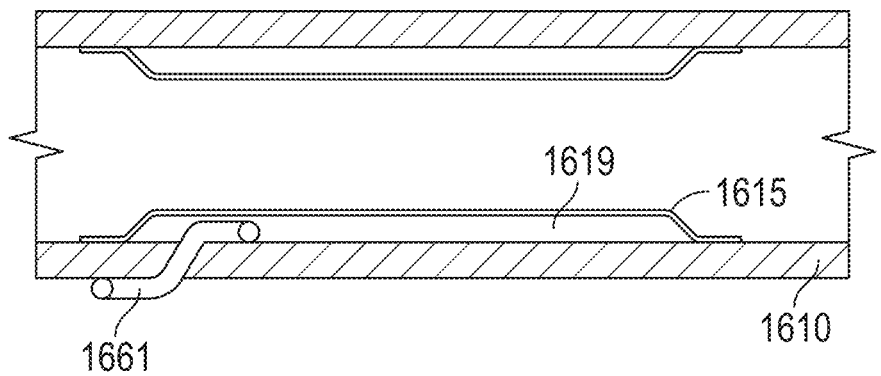
FIGS. 16A-16C show a bridge tube for inflation of an integral balloon.
Figure 16B:
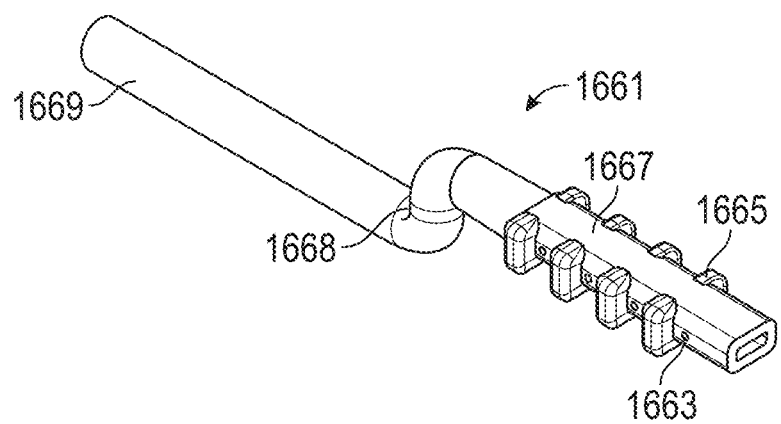
Figure 16C:
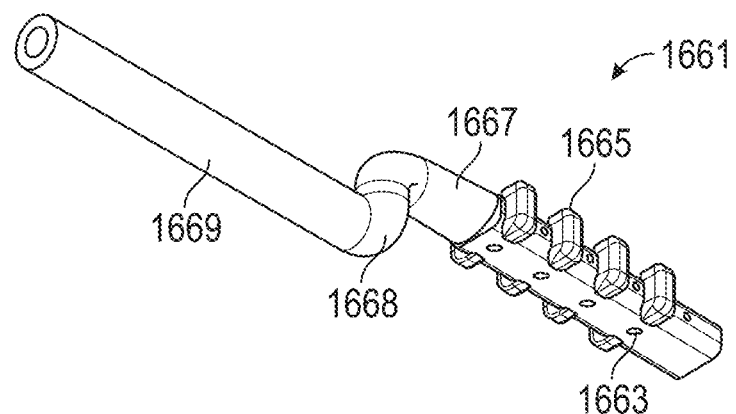

Referring to FIGS. 16A-16C, in some embodiments, an inflation bridge tube 1661 can be used to attach the inflation lumen of the catheter with the gap 1619 between the liner and the stent 1610. The bridge tube 1661 can have a distal portion 1667 positioned in the gap 1619, a proximal portion 1669 positioned along the exterior of the stent 1610, and a jog portion 1668 connecting the proximal portion and distal portion 1667, 1669 and extending through the wall of the stent 1610. The jog 1668 can be configured such that the distal portion 1667 and the proximal portion 1668 are offset, but substantially parallel with one another. Further, the proximal portion 1669 can be configured to attach to or be continuous with the inflation lumen while the distal portion 1667 can include a plurality of inflation holes 1663 configured to provide for the transmission of inflation fluid therethrough. In some embodiments, the distal portion 1667 can further include a plurality of projections 1665 (or stand-offs) proximate to the holes 1663 and configured to prevent the liner or other parts of the balloon from collapsing into the holes 1663. The projections 1665 can, for example, extend laterally from two, three, or four sides of the bridge tube 1661. In some embodiments, the inflation bridge tube 1661 may not include projections. In some embodiments, the distal portion 1667 can extend substantially the entire axial length of the balloon. The inflation bridge tube 1661, with the plurality of holes (and optionally the projections) can advantageously ensure quick inflation and deflation of the balloon.

The devices described herein can be configured to pump (e.g., inflate and deflate) to move blood in the antegrade direction and increase the flow rate of blood through the kidneys. In some embodiments, the pumping frequency can be approximately 0.5 to 3 times the normal heart rate, i.e., about 30-240, such as 60-180 inflations/deflations per minute. In some embodiments, the pumping frequency can be timed with the patient's electrocardiogram (ECG) so as to pulse in sync with the heart. For example, the frequency can be in sync with a pulse wave that occurs in the infrarenal aorta.

In any of the embodiments described herein, the device may include one or more sensors. In some embodiments, the sensor(s) is a pressure sensor to monitor, for example, the pressure gradient across the length of the device. The sensors can be positioned, for example, near the tip of the catheter and/or at or near the inlet and/or outlet of the covered stent. In some embodiments, the sensor(s) include one or more flow rate sensors to monitor, for example, the flow rate through the device.

In some embodiments, pressure and/or flow sensors can be built into the catheter in order to provide feedback to the physician or to the balloon inflation controller.

In some embodiments, the devices described herein can be configured to be removed from a patient's blood vessel immediately after a renal decongestion procedure. In some embodiments, the devices can be configured to be left in a patient's blood vessel so as to pump blood therethrough for a period of time, e.g., can be left in the vessel for between 3 hours and 3 days.

Any elements of any of the embodiments of the devices described herein can be used in addition to, or in place of, any of the elements of other embodiments of the devices described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the FIGS. is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for renal decongestion comprising:
   a hollow covered stent body having a first end and a second end;
   a first one-way valve at the first end of the hollow covered stent body;
   a second one-way valve at the second end of the hollow covered stent body;
   a balloon within the hollow covered stent body between the first one-way valve and the second one-way valve, the balloon configured to repeatedly deflate to pull blood through the first one-way valve into the hollow covered stent body and inflate to push blood through the second one-way valve from the hollow covered stent body in an antegrade direction; and
   a catheter connected to the hollow covered stent body.

2. The device of claim 1, wherein the balloon is an integral part of a liner positioned along an inner circumference of the hollow covered stent body.

3. The device of claim 2, wherein the liner is sealed at proximal and distal edges of the hollow covered stent body.

4. The device of claim 2, wherein the liner is positioned along the entire inner circumference of the hollow covered stent body.

5. The device of claim 1, further comprising an inflation lumen fluidically coupled with the balloon.

6. The device of claim 1, wherein the balloon is configured to inflate at a frequency of at least 0.5 to 3 times a normal heart rate.

7. The device of claim 1, wherein the balloon is configured to inflate at a frequency of about 30-180 inflations and deflations per minute.

8. The device of claim 1, further comprising an occlusion balloon positioned along the catheter.

9. The device of claim 1, wherein the hollow covered stent body is configured to transition between an expanded state and a collapsed state.

10. The device of claim 1, wherein the inflated balloon comprises a plurality of lobes.

11. The device of claim 1, wherein the hollow covered stent body is self-expandable.

12. The device of claim 1, wherein the catheter is positioned along an outer circumference of the hollow covered stent body.

13. The device of claim 1, wherein the catheter comprises an inflation lumen.

14. The device of claim 1, further comprising a second catheter, wherein the second catheter comprises an inflation lumen.

15. The device of claim 1, wherein the device comprises a plurality of balloons.

* * * * *